US 8,858,435 B2

(12) United States Patent
Liljeryd et al.

(10) Patent No.: US 8,858,435 B2
(45) Date of Patent: *Oct. 14, 2014

(54) METABOLIC MONITORING, A METHOD AND APPARATUS FOR INDICATING A HEALTH-RELATED CONDITION OF A SUBJECT

(75) Inventors: Lars Gustaf Liljeryd, Solna (SE); Ulf Frederik Magnusson, Solna (SE)

(73) Assignee: Diabetes Tools Sweden AB, Stockholm (SE)

( * ) Notice: Subject to any disclaimer, the term of this patent is extended or adjusted under 35 U.S.C. 154(b) by 1118 days.

This patent is subject to a terminal disclaimer.

(21) Appl. No.: 12/842,831

(22) Filed: Jul. 23, 2010

(65) Prior Publication Data

US 2011/0166791 A1 Jul. 7, 2011

Related U.S. Application Data

(60) Division of application No. 11/467,476, filed on Aug. 25, 2006, now Pat. No. 7,878,975, which is a continuation of application No. PCT/EP2005/002006, filed on Feb. 25, 2005.

(30) Foreign Application Priority Data

Feb. 26, 2004 (SE) ...................................... 0400456
Sep. 7, 2004 (SE) ...................................... 0402139

(51) Int. Cl.
*A61B 5/145* (2006.01)
*A61B 5/02* (2006.01)
(Continued)

(52) U.S. Cl.
CPC ........... *A61B 5/4866* (2013.01); *A61B 5/14532* (2013.01); *A61B 5/024* (2013.01);
(Continued)

(58) Field of Classification Search
USPC ......... 600/309, 316, 319, 345, 347, 365, 483, 600/485–499
See application file for complete search history.

(56) References Cited

U.S. PATENT DOCUMENTS 5,795,305 A 8/1998 Cho et al.
(Continued)

FOREIGN PATENT DOCUMENTS

EA           002288 B1    2/2002
JP          2002-501802   1/2002
(Continued)

OTHER PUBLICATIONS

Medik, V.A., et al., "Statistics in Medicine and Biology," vol. 1, 2000, Moscow, The Medicine Publishing House, pp. 180-183. (English Translation included).

*Primary Examiner* — Navin Natnithithadha
*Assistant Examiner* — Meredith Weare
(74) *Attorney, Agent, or Firm* — Michael A. Glenn; Perkins Coie LLP

(57) ABSTRACT

An apparatus for indicating a health-related condition of a subject has an input interface for receiving a sequence of samples of a first biological quantity derived by a first measurement method, the first measurement method being an invasive measurement and having a first impact on the subject, and for receiving a sequence of samples of a second biological quantity derived by a second measurement method, the second measurement method being a non-invasive measurement and having a second impact on the subject, wherein the first biological quantity gives a more accurate indication of the health-related condition of the subject than the second biological quantity, wherein the first biological quantity and the second biological quantity have a correlation to the health-related condition of the subject, and wherein the second impact is smaller than the first impact; a predictor for providing, for a certain time, for which no sample for the first biological quantity exists, an estimated value of the first biological quantity using samples for the first biological quantity and, as far as available, samples for the second quantity; and an output interface for outputting the estimated value or data derived from the estimated value so that an indication for the health-related condition of the subject is obtained.

24 Claims, 15 Drawing Sheets

(51) Int. Cl.
  *A61B 5/00* (2006.01)
  *A61B 5/0205* (2006.01)
  *A61B 5/024* (2006.01)
  *A61B 5/22* (2006.01)
  *A61B 5/021* (2006.01)

(52) U.S. Cl.
  CPC ................. *A61B 5/222* (2013.01); *A61B 5/021* (2013.01); *A61B 5/0205* (2013.01)
  USPC ........... 600/365; 600/347; 600/483; 600/485; 600/509

(56) References Cited

U.S. PATENT DOCUMENTS

| | | |
|---|---|---|
| 5,823,966 A | 10/1998 | Buchert |
| 6,151,517 A | 11/2000 | Honigs et al. |
| 6,572,542 B1 | 6/2003 | Houben et al. |
| 2001/0029326 A1* | 10/2001 | Diab et al. .................... 600/364 |
| 2004/0018486 A1 | 1/2004 | Dunn et al. |
| 2004/0167418 A1 | 8/2004 | Nguyen et al. |
| 2005/0043598 A1 | 2/2005 | Goode et al. |
| 2005/0107710 A1 | 5/2005 | Nakayama |
| 2005/0137470 A1 | 6/2005 | Rosenthal |
| 2005/0187720 A1* | 8/2005 | Goode et al. .................... 702/22 |
| 2005/0203360 A1* | 9/2005 | Brauker et al. ................ 600/345 |
| 2008/0183082 A1 | 7/2008 | Farringdon et al. |

FOREIGN PATENT DOCUMENTS

| | | | | |
|---|---|---|---|---|
| JP | 2003-508746 | 3/2003 | | |
| JP | 2003-524761 | 8/2003 | | |
| RU | 2180514 C1 | 3/2002 | | |
| RU | 2198586 C2 | 2/2003 | | |
| WO | WO99/39627 | 8/1999 | | |
| WO | WO 00/22413 A1 * | 4/2000 | ............ | G01N 15/06 |
| WO | WO 01/16579 A1 * | 3/2001 | ............ | G01N 21/35 |

* cited by examiner

METABOLIC MONITORING, A METHOD AND APPARATUS FOR INDICATING A HEALTH-RELATED CONDITION OF A SUBJECT

CROSS-REFERENCE TO RELATED APPLICATION

This application is a divisional of co-pending U.S. patent application Ser. No. 11/467,476, filed on Aug. 25, 2006, which is a continuation of co-pending International. Application No. PCT/EP2005/002006, filed Feb. 25, 2005, which designated the United States, and was not published in English, which claims priority to Swedish Patent Application No. 0400456-0, filed on Feb. 26, 2004 and Swedish Patent Application No. 0402139-0, filed on Sep. 7, 2004, each of which is incorporated herein by reference in its entirety.

BACKGROUND OF THE INVENTION

1. Field of the Invention

The present invention relates to improved interpretation of noisy physiologic and biochemical signals by the use of filtering, prediction and trend analysis of patient data, and discloses a method and device and/or a computer program product that aims at improving motivation, self-control and self-management of patients having type 2-diabetes or diabetes-related disease. The invention monitors oxygen utilisation of the heart, thus physical condition and fitness, and indicates stimulants and drug abuse and psychological and emotional stress. The invention discloses the use of a painless, non-invasive surrogate measure for blood glucose, as well as blood glucose prediction by sparse blood sampling, and a metabolic performance indicator. The invention offers long-term, metabolic monitoring at low cost combined with ease of use, and creates patient awareness of metabolic system function relating to the disease in an intuitive way, needing very little effort by the user. Lower cost, a lower burden for the health care system, prolonged lifespan and increased quality of life for the patient may be gained from the use of the proposed invention.

2. Description of Prior Art

Physiologic and biochemical signals for example blood glucose sampling, blood pressure and other monitored signals of mammalians can be very noisy, having a high variance when sampled over time. It is therefore critical to reduce such noise before accurate interpretation of the data can be made. Further, biochemical signals are often invasive in nature and such measurements can be discomfortable, costly or complicated to apply. The proposed invention strives to improve accuracy in interpretation of such signals by the use of suitable filtering methods and to reduce discomfort and cost by the use of non-invasive surrogate measures.

Diabetes is increasing globally in epidemic proportions and stands for a massive cost burden of healthcare. Type 1-diabetes, stands for around 10% of all diabetes cases. Type 2-diabetes, therefore stands for around 90% of all diabetes cases, and is steadily increasing. In the United States alone, it is estimated that up to 7% of the population may have diabetes. 100 million individuals are overweight, thus at high risk for type 2-diabetes. If this trend continues, 100% of the US adult population will be obese in year 2030. Total yearly cost of diabetes in the US including indirect costs where 1997 estimated to approximate USD 100 billion. In Saudi Arabia it has been estimated that up to 25% of the population may have diabetes related disease. The World Health Organization (WHO) predicts an increase to 300 million diabetes patients worldwide by the year 2025. Various attempts have been made to reverse this global epidemic trend, but to date this has failed.

Type 1-diabetes, (earlier referred to as insulin dependent diabetes mellitus IDDM), is identified by irreversible beta-cell destruction, that usually results in absolute insulin deficiency. Type 2-diabetes, (earlier referred to as non-insulin dependent diabetes mellitus, NIDDM), is identified as a heterogeneous disorder believed to involve both genetic and environmental factors. Type 2-diabetes is to a great extent a lifestyle related disease where modern sedentary lifestyle in combination with poor eating habits is believed to be major sources of the problem. The type 2-diabetes patient typically does not require insulin treatment for survival. The typical symptoms of type 2-diabetes are: Thirst, frequent urination, drowsiness, fatigue, overweight, gustatory sweating, varying blurred vision, elevated blood sugar levels, acetone breath and sugar in the urine. An examination of the patient will quite typically reveal a sedentary lifestyle and a distinct preference for a diet high in saturated fats and refined carbohydrates.

Insulin resistance is a common metabolic abnormality that characterizes individuals with various medical disorders including type 2-diabetes and obesity and occurs in association with many cardiovascular and metabolic abnormalities. Insulin resistance is defined as the inability of the body to respond adequately to insulin. The Syndrome-X or Metabolic Syndrome, also named the Insulin Resistance Syndrome, is a cluster of metabolic and physiologic risk factors that predict the development of type 2-diabetes and related cardiovascular diseases. It is generally characterized by five major abnormalities; obesity, hypertension, insulin resistance, glucose intolerance and dyslipedaemia. The prevalence rate of the metabolic syndrome in western countries is 25-35%. Aging is generally associated with insulin resistance and deteriorating beta cell function and obesity with insulin resistance and hyperinsulinemia.

Diabetic autonomic neuropathy (DAN) is a serious and one of the most common complications of diabetes. Most type 2-diabetes patients die in cardiovascular diseases preceded by a deterioration of the functionality of the autonomic nervous system (ANS). This is seldom noticed at an early stage, making type 2-diabetes a "stealth" disease developing slowly over the years and is most often unnoticed by the patient until discovered at a late stage. DAN impairs the ability to conduct normal activities of daily living, lowers quality of life, and increases the risk of death. DAN affects many organ systems throughout the body e.g., gastrointestinal, genitourinary, and cardiovascular. DAN is a result of nerve fibre destruction and loss related to the "toxic" effects of elevated blood glucose levels. Intensive glycaemic control is therefore critical in preventing the onset and slowing the progression of DAN. ANS problems and DAN can successfully be detected by the assessment of heart rate variability (HRV) analysis.

Hypertension is a major health problem in the western population and associated to cardiovascular disease. Arterial stiffening may be both a cause and consequence of hypertension, however recent research suggests that arterial stiffening is the typical precursor to hypertension, and that arterial stiffening is likely to have a genetic basis. The majority of type 2-diabetes patients (over 50%) suffer from hypertension. It is therefore imperative to control the blood pressure of diabetic patients. In type 2-diabetes it is recommended to keep the blood pressure below 130/80 either by improving life-style or by medication or a combination of both.

Insulin resistance and type 2-diabetes are associated with changes in plasma lipoprotein levels. Up to 70% of patients with type 2-diabetes have lipid disorders. Coronary heart disease is the leading cause of death among patients with type 2-diabetes. Dyslipidemia, together with obesity, hypertension, and hyperglycemia contribute strongly to coronary heart disease. Even mild degrees of dyslipidemia may elevate coronary heart disease risk factors. As these risk factors are additive or even multiplicative, strategies for lifestyle improvement should not only focus on hyperglycemia but also on dyslipidemia. As dyslipidemia in type 2-diabetes usually show smaller and denser LDL-particles, which are more atherogenic, the target for cholesterol lowering should include very-low-density lipoprotein (VLDL) and low-density lipoprotein (LDL) as well as lowering of elevated triglycerides (TG).

Mental stress, elevated blood-pressure and elevated heart rate are common problems of today's society. Modern work and lifestyle is less physically active where hi-tech related jobs often result in a sedentary lifestyle. High demand work with sustained high levels of stress is common and a negative effort/reward factor can contribute to stress induced disease. It is well known that mental stress can influence metabolism such as elevated blood-glucose levels as well as an increased systolic blood pressure and heart rate. Various stimulants such as caffeine, nicotine, alcohol, cocaine and amphetamine also increase systolic blood pressure and heart rate.

Modern type of diet, high in energy and fat content is associated with insulin resistance and related disorders. The exact aetiology of insulin resistance is however not clear. Genetic predisposition and environmental factors including quality and quantity of dietary fat, both contribute to development of an inability to adequately dispose plasma glucose at normal plasma insulin levels. Fast food outlets are gaining popularity due to high sugar, fat-rich and tasty food in combination with time-efficient eating. The increased consumption of fast-acting, high-energy carbon hydrates reflects in blood sugar overshoots and insulin overshoots followed by blood sugar undershoots and drowsiness, again demanding renewed intake of fast-acting carbon hydrates etc. This cyclic feedback is frequently pounding the metabolic regulatory system. Such transient excitation is believed in the long term to be harmful and contribute to insulin resistance and elevated insulin levels, the early start-up of the type 2-diabetes process. The above life-style related problems are currently creating health problems of a magnitude unheard of in the past.

Physical activity, thus aerobic fitness is the cornerstone in fighting type 2-diabetes related disease. It is a most important task to improve cardiovascular fitness by physical activity that increases the capability and efficiency of the heart to supply the cardiovascular system with oxygen as well as improve insulin sensitivity and oxygen uptake of the muscles. The heart functions like any muscle that it can be trained to become stronger and more efficient. A weight reduction by only 10% usually shows positive effects on blood glucose and lipid levels. In particular, it is important to reduce abdominal fat mass.

Physical activity and energy expenditure can be estimated in a variety of ways that do not constrain the patient during his normal daily activities. Different methods exist like pedometers, accelerometers, heart-rate meters etc. One popular method use a pedometer to calculate number of steps walked or approximate the calories so consumed by a simple formula. Others calculate energy expenditure in relation to body movement and acceleration by the use of single-axial, bi-axial or tri-axial accelerometers. Another method use pulse monitoring based on plethysmograps, (a device that shines light through a finger or earlobe to calculate heart rate and physical activity). One other popular device, a pulse watch, measures the EKG signal by the use of a chest-strap with electrodes and transmits the EKG pulses to a specially designed wrist-watch calculator, which can calculate calories consumed and other parameters related to physical activity. However the simplest way to quantify physical activity is to just roughly estimate the daily activity, for example on a scale from one to five, relating to the daily effort made and the intensity and duration of the physical activity performed. More elaborate calculation and reporting methods include the MET tables (metabolic equivalent) or formula, which is an accurate index of the intensity of physical activity. Modern inactive and sedentary lifestyle has opened up a large market for health gymnasiums and marketing of various health-related products, and physical training programs for the improvement of physical fitness. Despite this positive trend, type 2-diabetes related disease is rapidly increasing at an alarming rate.

It is difficult to motivate high-risk, overweight, sedentary and diabetes-prone individuals to change life style. Just informing the individual of the health-risks involved and the need of physical training and/or the need for corrected eating habits and/or de-stressing treatment is often not sufficient. Low fit individuals often do not feel comfortable by being examined by somebody else or being forced to exercise training in gymnasiums. It is common to find overweight individuals embarrassed by their low physical fitness level, and in order to avoid humiliation, refuse to join rehabilitation programmes. It is believed by the inventor that the only way to break such detrimental trend is to educate people by hands-on experience by the use of simple and intuitive tools to monitor their own metabolic function, preferably at home in private. The individual can then himself gain understanding of the problems involved and gain insight to what extent and intensity it is necessary to change lifestyle.

Self monitoring using a personal blood-glucose meter is usually necessary for type 1 insulin dependent diabetes mellitus (IDDM) patients in order to aid self-administration of insulin. However it is less common that blood-glucose monitoring is prescribed for patients with manifest or borderline type 2-diabetes. Self-monitoring using urine dipsticks for urine-glucose measurements are more or less obsolete today and seldom used due to the fact that the renal threshold varies individually over a wide range. In addition this method cannot measure glucose levels below the renal threshold, exhibits long delay and low sensitivity, and therefore the use of blood-glucose monitoring is preferred.

Recent research has reported some benefits of using a blood-glucose meter for BG-monitoring in connection with meals for patients with type 2-diabetes. The idea is to monitor pre-prandial and post-prandial glucose levels to gain knowledge of the metabolic effect of the meal on the patient. The patient can then learn by experience how the glucose level will raise post-prandially and give him feedback on the glucose variation relating to different types of food intake. The idea is to balance the food intake, where a reduction in refined fast acting carbohydrates will reduce post-prandial blood-glucose overshoots. Such overshoots are understood to cause long-term damage to the autonomic nervous system and eventually may lead to diabetes and diabetic neuropathy. Such form of self-monitoring is cumbersome and impractical to maintain and it is not uncommon that patients drop out of such test trials due to lack of motivation relating to the intensity of the method. Blood glucose meters and tools need to be carried around by the patient during the day and testing is sometimes disclosed in public when having a meal in a restaurant. Including such cumbersome procedures as part of a patient's long-term daily practice is not very likely to succeed. In addition the cost is not negligible according to the consumption of a number of blood-glucose sticks and a number of finger-puncturing lances during the day. In addition, although such test is minimally invasive in nature it can be painful and very uncomfortable to the patient. Further it gives little room for logic and intuitive interpretation of the results and it is therefore difficult to comprehend and administer for the patient in order to obtain a therapeutic goal, a serious disadvantage.

The World Health Organisation (WHO) and American Diabetes Association (ADA) has specified blood-glucose ranges and levels in order to differentiate between the different stages of diabetes. Fasting glucose concentrations that diagnose the symptomatic patient (WHO criteria, 1999) are shown below. Fasting sample glucose concentrations are in mmol/L:

|  | Whole Blood | | Plasma | |
|---|---|---|---|---|
|  | Venous | Capillary | Venous | Capillary |
| Manifest Diabetes Mellitus | >6.1 | >6.1 | >7.0 | >7.0 |
| Impaired glucose tolerance (IGT) | <6.1 | <6.1 | <7.0 | <7.0 |
| Impaired fasting glucose (IFG) | 5.6-6.0 | 5.6-6.0 | 6.1-6.9 | 6.1-6.9 |
| Normal | <5.5 | <5.5 | <6.0 | <6.0 |

When assessing blood-glucose levels in the clinic, it is unfortunately quite common to overlook the existence of a strong biologic variability as well as an analytic variability. Thus substantial variability exists between observations that may be misinterpreted by the inexperienced physician resulting in reduced accuracy in grading and diagnosis of the disease.

When a blood sample is drawn in a clinic, a number of factors influence the accuracy of the measurement result such as:

1. Sub-optimum calibration of the clinical analysis instrument. See a practical example in FIG. 1.
2. Aging of the blood sample by glycolysis, as glucose preservatives does not totally prevent glycolysis.
3. "White-Coat Hyperglycemia", elevated BG value due to a nervous "needle-phobia" patient. See a practical example in FIG. 2.
4. A continuously falling fasting BG value, related to increasing time of day.
5. A time-variable insulin sensitivity, thus different sensitivity from day to day.
6. Female cyclic hormonal changes due to menstruation.
7. BG can vary due to transitory acute infections, traumatic stress and even a simple cold or flu.

Relating to the above uncertainties, it is believed by the inventor that blood-glucose monitoring under controlled conditions in the home, using a sufficiently accurate blood-glucose meter together with suitable post-processing and filtering methods, improves the accuracy of the diagnostic classification. This is believed by the inventor, to be superior compared to established clinical laboratory measurements and current praxis.

Although elevated insulin levels (hyperinsulinemia) appears in the bloodstream long before elevated blood glucose levels eventually manifest; yet a high glucose level remains the classic type 2-diabetes symptom classifier. Insulin levels are rarely, if ever, used as a diabetic risk marker or diagnostic tool except for clinical research purposes, a remarkable fact. Thus, a low blood glucose level does not preclude the presence of the disease.

Monitoring of oxygen saturation is common practice of patients under emergency treatments as well as in the operating theatre. Before the invention of the now widely used pulse-oximeter, (an instrument that monitors blood haemoglobin oxygen saturation using infrared light absorption), it was common practice to calculate the Rate-Pressure-Product (RPP) of the patient during surgery to establish the patients heart condition and oxygen utilization. The RPP (also called the Double Product) is a reasonably accurate measure of heart oxygen utilization and is derived by multiplying the systolic blood pressure by the heart rate (RPP=sBP×HR/100). After the introduction of the pulse oximeter, RPP has found little use today, but has some use in sports medicine indicating oxygen consumption of the heart during treadmill exercise tests etc. RPP also indicate stress and the use of stimulating drugs.

In order to ease the burden for the patient, the inventor declares that only fasting blood glucose sampling is necessary for accurate long term monitoring and treatment of type 2-diabetes related disease. Even sparsely sampled blood glucose measurements for example once a week may be sufficient, relating to an embodiment of the invention for an accurate prediction of daily BG. More intensive and cumbersome blood glucose monitoring like pre- and postprandial blood glucose measurements during the day is not deemed necessary as the fasting blood glucose level generally indicates the relative magnitude of postprandial blood glucose excursions. Thus a higher fasting blood glucose level is reflected in a higher postprandial blood glucose level and vice versa. This can be indicated by the use of multiple three-sample oral glucose tolerance OGTT tests sampled at 0 h, 1 h and 2 h during an intervention lifestyle improvement period see FIG. 3. It can be seen that as life-style is improved with lower fasting BG, also the postprandial BG-values follows the declining trend. However, 1 h post-prandial BG measurements may of course be used as an alternative to fasting BG when deemed necessary. This is however more cumbersome and therefore less practical as explained above.

In an additional embodiment of the invention, the BG level is predicted from preferably blood pressure and heart rate (Rate Pressure Product) alone, making painful finger pricking or painful invasive procedures unnecessary except for the initial calibration and set-up procedure of the predictor. In another embodiment of the invention, it offers less frequent need of painful finger pricking.

The proposed invention offers the patient an intuitive way to measure and analyse certain physiologic parameters such as for example intensity of physical activity, blood-glucose, blood pressure and heart rate. In addition important patient data such as lipid levels, total cholesterol, triglycerides, body temperature, weight, body mass index and the waist to hip ratio can be stored and processed. Following such measurements, data is processed and optimised using suitable filtering algorithms, and thereafter indicated to the patient in an intuitive manner for instant feedback of his behaviour, progress and results.

A preferred embodiment of the invention comprises the following steps:

Estimating or measuring the level of physical activity on a preferably daily basis, and preferably collecting this information into a database.

Measuring the fasting and/or post-prandial blood-glucose level on a more or less frequent basis, densely or sparsely sampled, and preferably collecting this information into a database Measuring the systolic-diastolic and heart rate on a frequent basis, densely sampled, and preferably collecting this information into a database Calculate the rate pressure product from systolic blood pressure and heart rate.

Measure any other relevant physiological parameter such as body weight, body temperature, blood lipids etc and preferably collecting this information into a database Low-pass filter, enhance, error-correct and missing data-interpolate the above data using statistical and/or signal processing methods.

Apply prediction methods to predict blood glucose values from preferably the rate pressure product.

Combine and/or filter obtained data by suitable algorithms to noise-reduce, clarify and improve the so obtained information for presentation.

Present the processed, enhanced and/or predicted data as a trend to the patient in an intuitive and easy to understand manner for easy interpretation of patient parameters.

From the above, it becomes clear that metabolic monitoring of diabetes related disease is essential in order to assess at least the current status of a subject. Dense sampling of vital biological parameters offers several advantages. The main advantage is that the subject is continuously made aware of his current status so his health condition does not deteriorate. An other advantage is that the subject continuously receives an overview over any changes or trends in his current status, which may for example relate to a lack of physical activity or a lack of good nutrition in the worse case, or sufficient physical activity and a well-controlled diet in the better case. Yet another important advantage is that the subject gets instantaneous feedback of his status and can adjust his lifestyle according to the developing trend. The prerequisite for efficient metabolic monitoring according to the invention is that the subject monitors vital biologic parameters. For example blood glucose levels, blood pressure and heart rate can be measured at wake-up in the morning and physical activity can be measured during the day etc.

Accurate blood glucose monitoring requires invasive measurements, although finger pricking may be considered as minimally invasive. Currently there is no other method that can compare in accuracy to an invasive measurement. A subject pricks his finger to sample a small amount of blood, which is subsequently examined in an analytical device, which outputs a blood glucose value. Even minimally invasive methods are costly, and often experienced as discomfortable and can thus have a negative impact on the patient and disease management.

SUMMARY OF THE INVENTION

It is an object of the present invention to provide an improved concept for indicating a health-related condition of a subject, which is easier to comprehend, offers lower running cost, is more comfortable and more motivating for the subject to use, compared to traditional methods.

In accordance with a first aspect, the invention provides an apparatus for indicating a health-related condition of a subject, having:
an input interface for receiving a raw sequence of samples of a first biological quantity derived by a first measurement method, the first measurement method being an invasive measurement and having a first impact on the subject, and for receiving a raw sequence of samples of a second biological quantity derived by a second measurement method, the second being a non-invasive measurement and having a second impact on the subject, the biological quantities having a useful variation and a non-useful variation;
wherein the first biological quantity gives a more accurate indication of the health-related condition of the subject than the second biological quantity, wherein the first biological quantity and the second biological quantity have a correlation to the health-related condition of the subject, and wherein the second impact is smaller than the first impact;
a predictor for providing, for a certain time, for which no sample for the first biological quantity exists, an estimated value of the first biological quantity as a predicted sample using samples for the second biological quantity and, as far as available, samples for the first quantity;
a filter for filtering a sequence having samples of the first biological quantity and at least one predicted sample, the filtered sequence having a useful variation and a reduced non-useful variation compared to the sequence before filtering, and
an output interface for outputting at least an increase indication, a decrease indication or a remain unchanged indication as a trend of the data, the trend being representative to a useful variation of the health-related condition of the subject.

In accordance with a second aspect, the invention provides a method of indicating a health-related condition of a subject, the method including the steps of:
receiving a raw sequence of samples of a first biological quantity derived by a first measurement method, the first measurement method being an invasive measurement and having a first impact on the subject, the first biological quantity having a useful variation and a non-useful variation;
receiving a raw sequence of samples of a second biological quantity derived by a second measurement method, the second measurement method being a non-invasive measurement and having a second impact on the subject, the second biological quantity having a useful variation and a non-useful variation;
wherein the first biological quantity gives a more accurate indication of the health-related condition of the subject than the second biological quantity, wherein the first biological quantity and the second biological quantity have a correlation to the health-related condition of the subject, and wherein the second impact is smaller than the first impact;
providing by prediction, for a certain time, for which no sample for the first biological quantity exists, an estimated value of the first biological quantity as a predicted sample using samples for the second biological quantity and, as far as available, samples for the first quantity; and
filtering a sequence having samples of the first biological quantity and at least one predicted sample, the filtered sequence having a useful variation and a reduced non-useful variation compared to the sequence before filtering; and
outputting at least an increase indication, a decrease indication or a remain unchanged indication as a trend of the data, the trend being representative to a useful variation of the health-related condition of the subject.

In accordance with a third aspect, the invention provides a computer program having a program code for performing a method of indicating a health-related condition of a subject, the method including the steps of:
receiving a raw sequence of samples of a first biological quantity derived by a first measurement method, the first measurement method being an invasive measurement and having a first impact on the subject, the first biological quantity having a useful variation and a non-useful variation;
receiving a raw sequence of samples of a second biological quantity derived by a second measurement method, the second measurement method being a non-invasive measurement and having a second impact on the subject, the second biological quantity having a useful variation and a non-useful variation;

wherein the first biological quantity gives a more accurate indication of the health-related condition of the subject than the second biological quantity, wherein the first biological quantity and the second biological quantity have a correlation to the health-related condition of the subject, and wherein the second impact is smaller than the first impact;

providing by prediction, for a certain time, for which no sample for the first biological quantity exists, an estimated value of the first biological quantity as a predicted sample using samples for the second biological quantity and, as far as available, samples for the first quantity; and filtering a sequence having samples of the first biological quantity and at least one predicted sample, the filtered sequence having a useful variation and a reduced non-useful variation compared to the sequence before filtering; and outputting at least an increase indication, a decrease indication or a remain unchanged indication as a trend of the data, the trend being representative to a useful variation of the health-related condition of the subject, when running on a computer.

The present invention strives to reduce discomfort and cost for the user by the introduction of new surrogate measures and prediction.

The present invention is based on the finding that a high accuracy invasive measurement method can be partly substituted by a surrogate non-invasive measurement method. The high accuracy invasive measurement method is typically represented by a costly, uncomfortable and "hard" measurement method, and where the non-invasive measurement method is a low-cost, comfortable and "soft" measurement method, relating to its impact on the subject.

The predictor generates densely sampled invasive data, based on sparsely sampled invasive data and densely sampled non-invasive data. Thus, the subject does not have to commit to painful finger pricking daily or as often as would be necessary in the prior art, but could revert to less frequent finger pricking as for example on a weekly basis. The subject only has to perform a simple and painless non-invasive blood pressure related measurement method on a for example daily basis, and this therefore does not have a large impact on the subject.

In another preferred embodiment, the predictor is fed with more than one biological quantity, which is derived from a non-invasive measurement.

In accordance with the present invention, the only prerequisite for the two measurements or biological quantities is that both measurements have a correlation to the health-related condition of the subject.

Further, the present invention strives to improve accuracy in the interpretation of noisy physiologic signals by the use of low-pass filtering methods for extraction of the useful signal variation and removal of non-useful signal variations.

BRIEF DESCRIPTION OF THE DRAWINGS

These and other objects and features of the present invention will become clear from the following description taken in conjunction with the accompanying drawing, in which.

DESCRIPTION OF PREFERRED EMBODIMENTS

Figure 21:
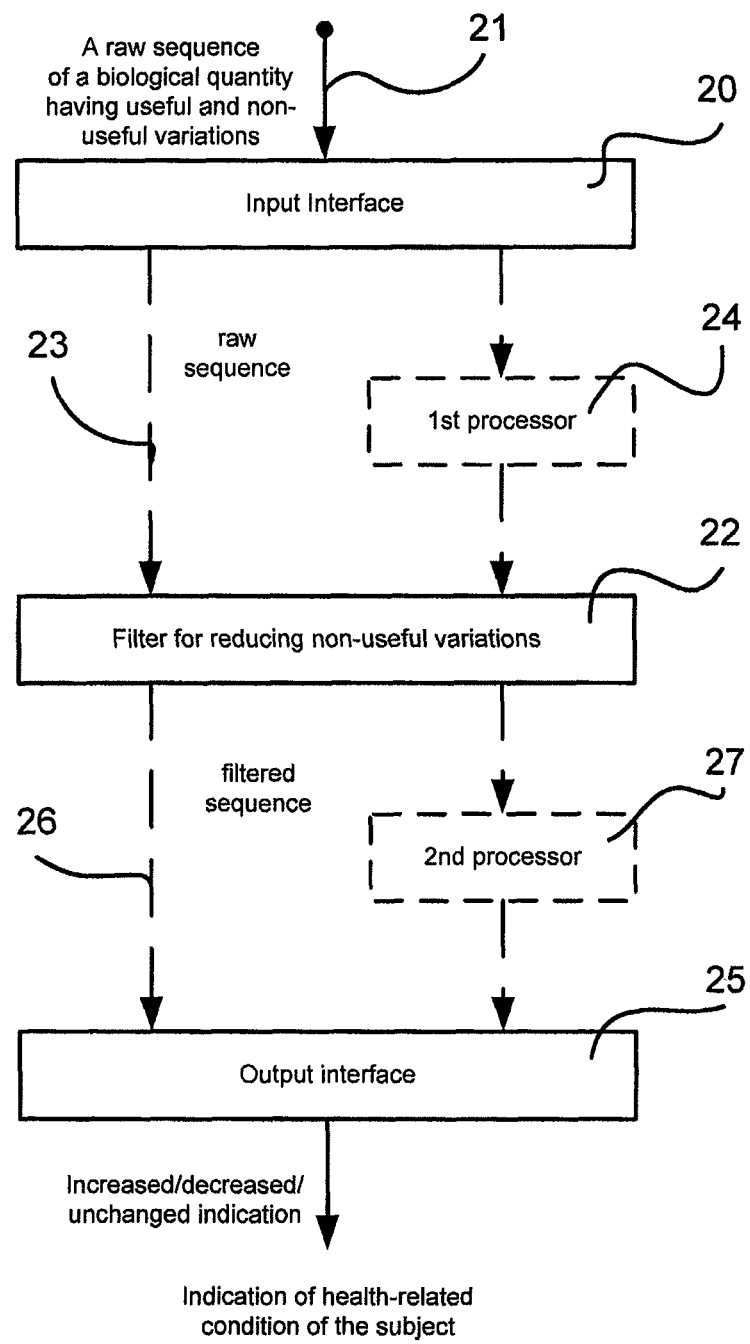
FIG. 21 is a block diagram of a filter/trend device.

FIG. 21 shows a block diagram for illustrating a filter/trend device, i.e., a block diagram for an apparatus for indicating a health-related condition of a subject. This apparatus includes an input interface 20 for receiving a raw sequence of samples of a biologic quantity related to the health condition of the subject, wherein the biological quantity has a useful variation and a non-useful variation (arrow 21 in FIG. 21).

Depending on the specific implementation, the input interface obtains these samples of the biological quantity, which forms the raw sequence, by a manual input such as via a keyboard, by cable, radio, infra-red or other means from an analytical device, which for example analyses a blood sample to output a blood glucose value, blood pressure, heart rate, physical activity or any other biological quantity of interest, to an electronic buffer, memory or similar means within the input interface 20. Thus, one obtains, at the output of the input interface 20, the raw sequence as a sequence of samples, which can be input to a filter device 22 as indicated by an arrow 23 connecting block 20 and block 22.

Alternatively, or additionally, the raw sequence can also be input into a first processor 24 for processing the raw sequence to obtain a processed sequence, which is, after being processed by the processor 24, filtered in the filter device 22.

The first processor 24 may include predictor, an interpolator or any other means, which is arranged to derive the processed sequence using the raw sequence output by block 20. In this connection, the first processor can also include, as will be outlined later, a combiner for combining two or more raw sequences to obtain a combined raw sequence, which can then be filtered by the filter device 22.

The filter 22 is arranged for filtering the raw sequence of samples or the processed sequence of samples derived from the raw sequence of samples to obtain a filtered sequence. It is to be noted here that the filter, which is preferably a low-pass filter, is configured for reducing the non-useful variation to obtain a filtered sequence, which has a stronger influence of the useful variation compared to the influence of the non-useful variation, or which can even be completely eliminated.

The apparatus further comprises an output interface 25 for outputting the filtered sequence or an enhanced sequence derived from the filtered sequence, wherein the output interface is arranged to output at least an increase indication, a decrease indication or a remain unchanged indication as a trend of the filtered sequence or the enhanced sequence, the trend being representative for a useful variation of the health-related condition of the subject. As it becomes clear from FIG. 21, the output interface 25 processes the filtered sequence output by the filter 22 directly as indicated by an arrow 26. Alternatively, the inventive apparatus further includes a second processor 27 for deriving the enhanced sequence using the filtered sequence. Depending on a certain environment, the second processor 27 can include a combiner as shown in FIG. 22a or can include any signal conditioning means such as an amplifier, etc. to modify the filtered sequence for obtaining an enhanced sequence which is to be output.

Figure 20:
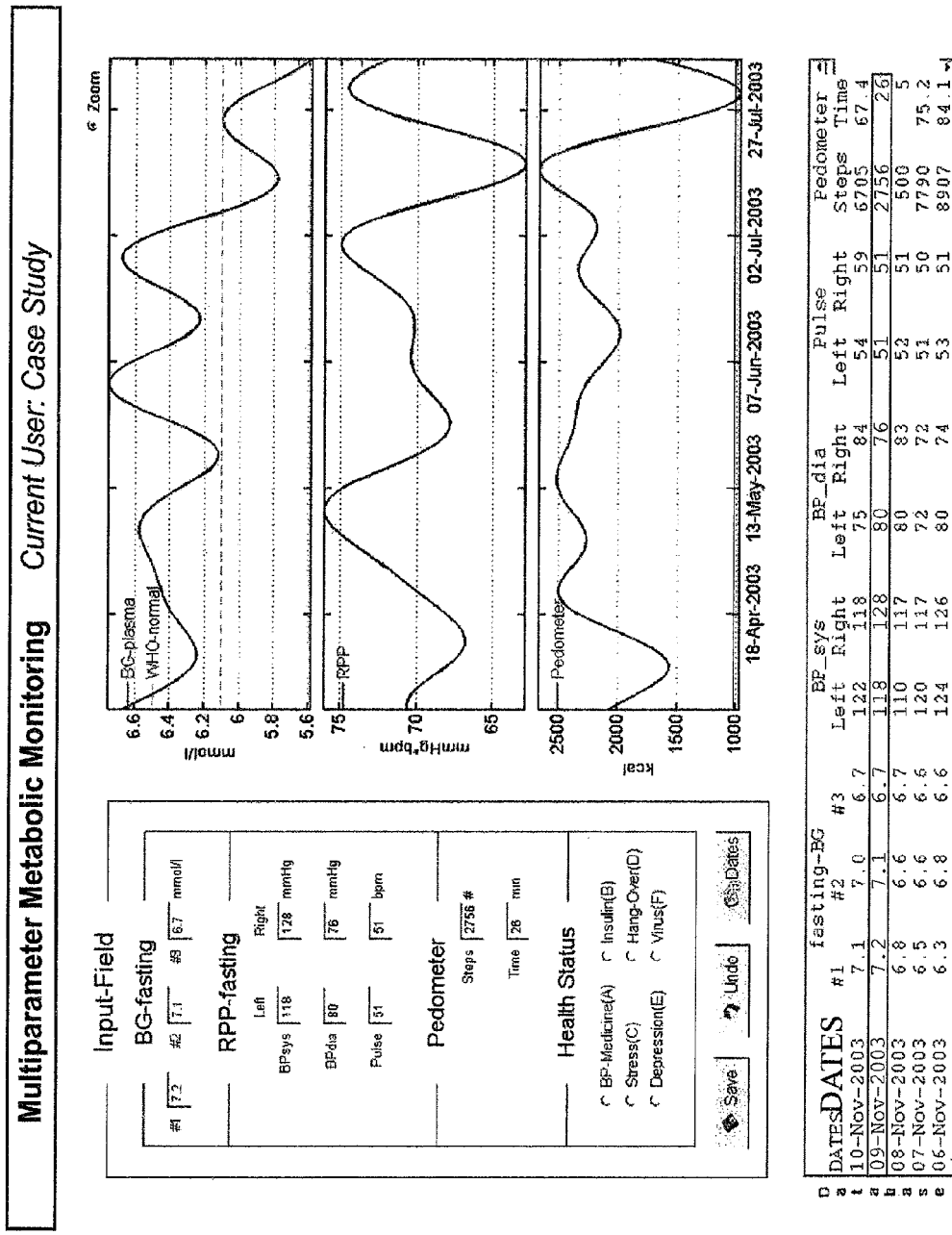
FIG. 20 shows a screen-dump of the first page of the computer program product.

With respect to the output interface 25, it is to be noted here that the trend indication can be, of course, a graphical display as shown in FIG. 20, showing a complete filtered or enhanced sequence. Alternatively, the output interface can also show simply the trend, by indicating an up-arrow or a coloured light or by other indicating means, when the trend is going up, or by indicating a down-arrow or a different coloured light or by other indicating means, when the trend is going down, or by doing nothing or indicating any other sign to indicate that there is a remain-unchanged indication.

Naturally, this can also be done by a sensory perceptive interface for example for the blind or deaf which outputs certain perceptive indications for indicating an increase, a decrease or a remain unchanged situation. Naturally, one can signal such an indication by mechanical means such as a sound or strong vibration for an increase, a week vibration for a decrease or a very weak vibration for a remain unchanged situation. Alternatively, the frequencies of the vibrations can be made different from each other for each indication. Alternatively, apart from vibration indication means, one can also use any other mechanical marking such as raising a key so that the raised key can be felt by a user compared to the situation, in which the key is not raised.

Figure 22A:
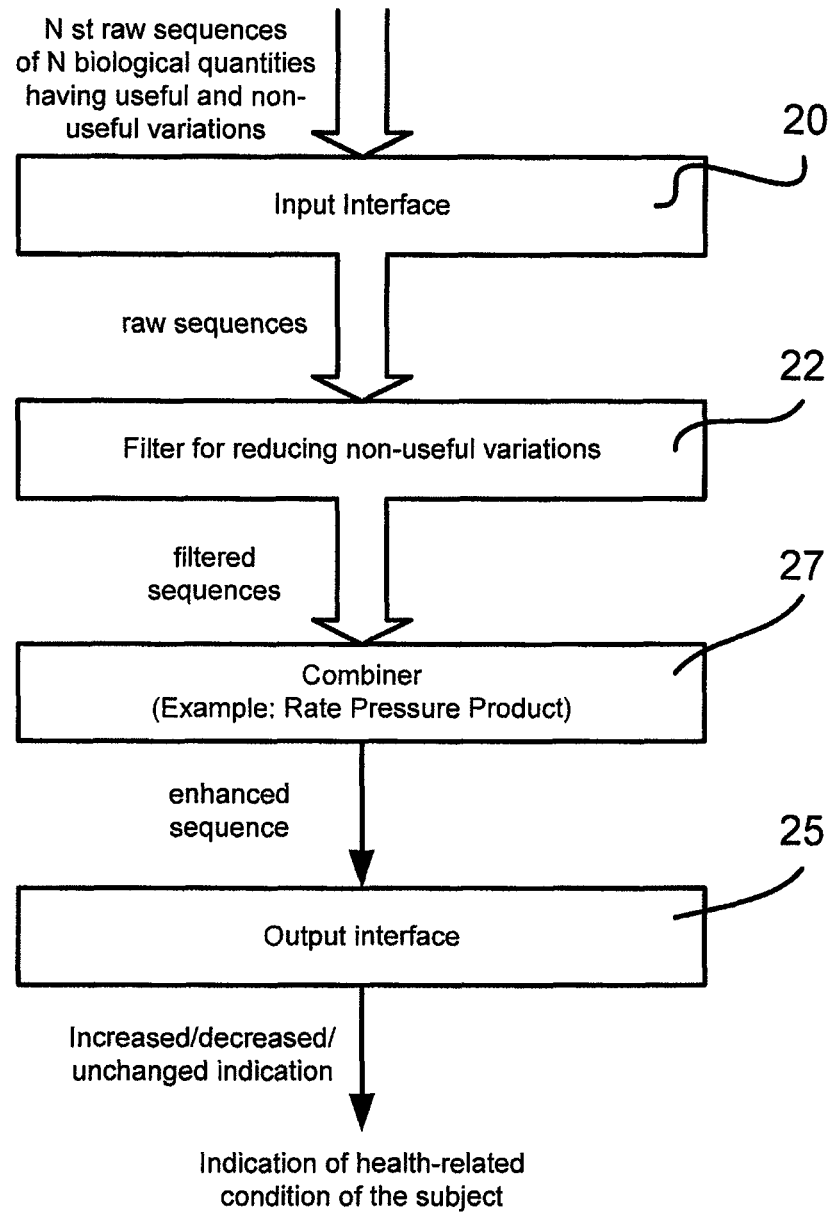
FIG. 22a is a block diagram of the FIG. 21 device having the second processor.

FIG. 22a shows an embodiment of the second processor 27 of FIG. 21. In this embodiment, the combiner is the sample-wise combiner to for example, multiply a sample of the filtered sequence of heart rate by a sample of the filtered sequence of the blood pressure to obtain the enhanced sequence representing the filtered rate-pressure product.

Figure 22B:
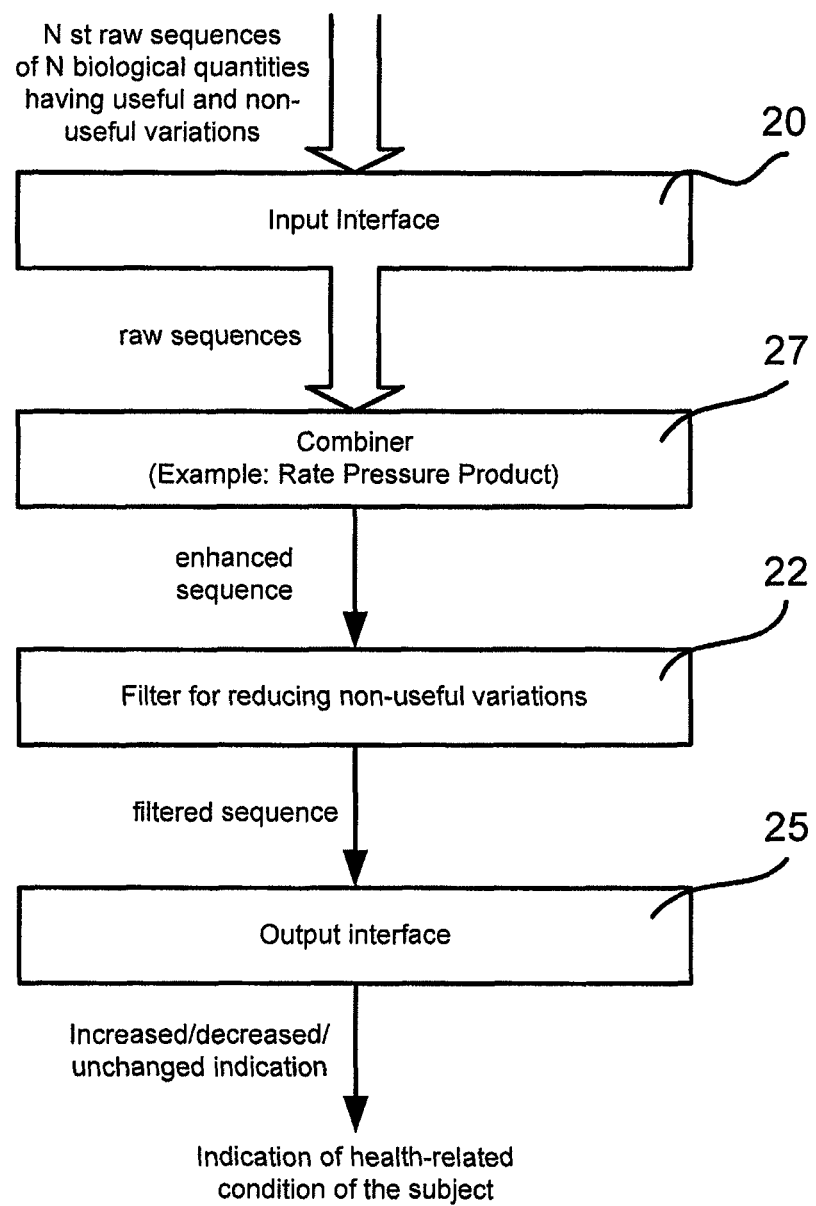
FIG. 22b is a block diagram of the FIG. 21 device having the first processor.

FIG. 22b indicates an embodiment of the first processor 24, but for the case, in which the blood pressure and the heart rate for example are combined, i.e., sample-wise multiplied before filtering. This means that the FIG. 22b embodiment illustrates forming of a raw rate-pressure product, which is, subsequently, filtered by the filter 22 to reduce the non-useful variations of the raw rate-pressure product.

Figure 17:
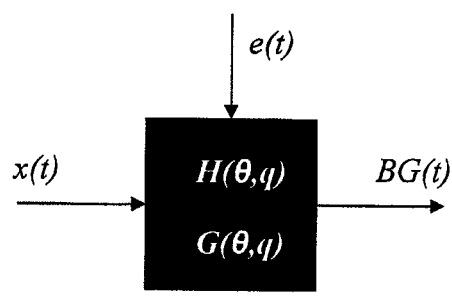
FIG. 17 shows that the system being identified can be represented by the black-box approach.
Figure 23:
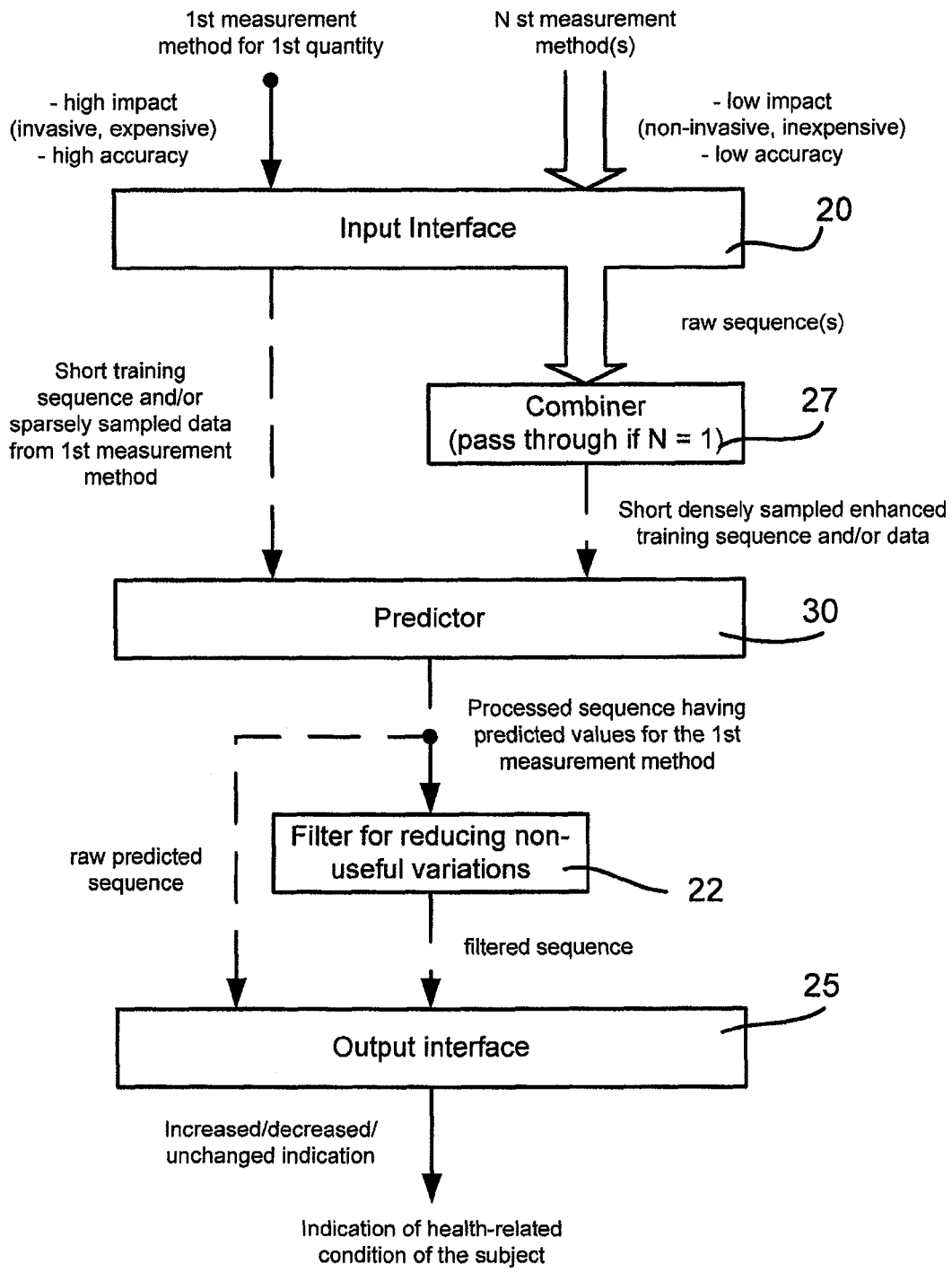
FIG. 23 is a block diagram of an embodiment of the present invention.

FIG. 23 shows the inventive device in accordance with the invention, which includes a predictor 30 for providing, for a certain time, for which no sample of the first biologic quantity exists, an estimated value of the first biological quantity. Preferably, a measurement value of an invasive measurement is predicted using one or more measurement values of a non-invasive measurement, as is outlined in detail in connection with FIG. 17 and FIG. 20. Depending on certain situations, the predictor can be a free-running predictor or a predictor, which is updated in regular or irregular intervals.

The present invention builds on the simple concept that "knowledge gives motivation" and encourages life-style improvement for the patient. The invention offers patient monitoring in a new way by the use of trend analysis, based on well-proven and traditional patient measurements, and presents new and improved ways of indicating patient status. Such improved information can be used by the patient and/or his doctor for treatment planning and follow-up. The invention motivates and educates the patient by the use of performance feedback, so he can make progress in his life-style modification.

In type 2-diabetes related disease, it is current practice for the doctor to inform the patient that a change of eating habits and lifestyle change is needed, but it is usually difficult for the patient to judge and comprehend the necessary level of change. It is often difficult to motivate the patient due to the "silent" nature of this disease. If the life-style modification is performed too aggressively, exhaustion and loss of motivation may result and the patient may give up. On the other hand, if it is not performed seriously enough, it will not have the desired effect. The benefit of the proposed invention is that the appropriate level of lifestyle change is clearly indicated to the patient in an intuitive way, thus avoiding discouraging over-efforts.

It is believed by the inventor that this, by the method indicated "just enough" level of approach, is the key to long-term motivation and success of rehabilitation. This is achieved using new multi-parameter physiological monitoring methods in combination with clear trend indications, thus encouraging self-control and rewarding the patient for good behaviour for the effort made, and give an negative indication when the patient fails to progress. Such instantaneous indication of performance feedback is far superior to, and in strict contrast to traditional medical practice using very long-term "feedback" given by the doctor on only a sparse per-visit basis.

The present invention describes a new method and/or a new device that needs a minimum of patient engagement and effort, where some patient parameters are frequently sampled, once a day or even once a week and other parameters are sampled less frequently. The frequently sampled parameters may easily be performed at bedside in the morning and no equipment or tools needs to be carried around during the day. The less frequently sampled patient parameters may be performed for example at the clinic.

Frequently sampled physiological patient parameters in a densely or sparsely manner, equidistant or non-equidistant sampled, may consist of:
Blood glucose
Physical activity
Blood pressure
Heart rate
Body temperature
Body weight
Body. Mass Index Substantially less frequently sampled patient parameters can consist of
HbA1c
Insulin
Lipids
Albumin levels
Other related parameters of interest When assessing blood-glucose levels at home it is important that the analytic variability of the measuring instrument is low and substantially less than the biological variability of the patient. Else the measurement will be meaningless. Unfortunately some personal-type blood-glucose meters have an unacceptably high analytic variability, making them less reliable and useful for accurate blood-glucose measurements. However some commercially available low-cost personal-type blood-glucose meters are found to be sufficiently accurate for reliable measurements of for example fasting BG, provided appropriate post processing of the data is performed. On the other hand if higher accuracy is wanted, for example two or more consecutive measurements within minutes can be performed, and subsequently averaged in a post-process. Multiple BG-meters can also be used in parallel to reduce variability and the results averaged. This can preferably be performed in clinical research when high accuracy is needed and has been used in the research to verify the proposed invention.

Due to the strong biologic variability of the blood glucose level in combination with some analytic variability of the blood glucose measuring instrument, substantial data scatter is experienced, making the noisy signal difficult to interpret. See FIG. 4, that demonstrates a typical fasting BG sequence spanning over approximately 10 months. Note the difficulty in diagnosing a patient accurately as the data is very noisy, thus showing high biologic variability. The data over time is scattered over a wide range, thus the patient BG is spanning from normal to diabetic values. If one counts the number of days that satisfy each WHO criteria for our case-study patient, we get an interesting graph, see FIG. 5. 37% of the 257 days evaluated the patient is fully normal. 57% of the days he has Impaired Fasting Glucose (IFG). 7% of the days he has manifest diabetes.

According to the above strong variability of BG, the inventor strongly believes that current diabetes criteria results in sub-optimum diagnosis and therefore needs to be revised. In order to make BG interpretation more accurate, low-pass filtering of multiple BG data is necessary. However, it is important not to filter the data too excessively, as this will reduce short-term variations and blunt the details of variation. Optimum filtration and avoidance of over-filtration can be obtained by residual analysis described later.

Figure 6:
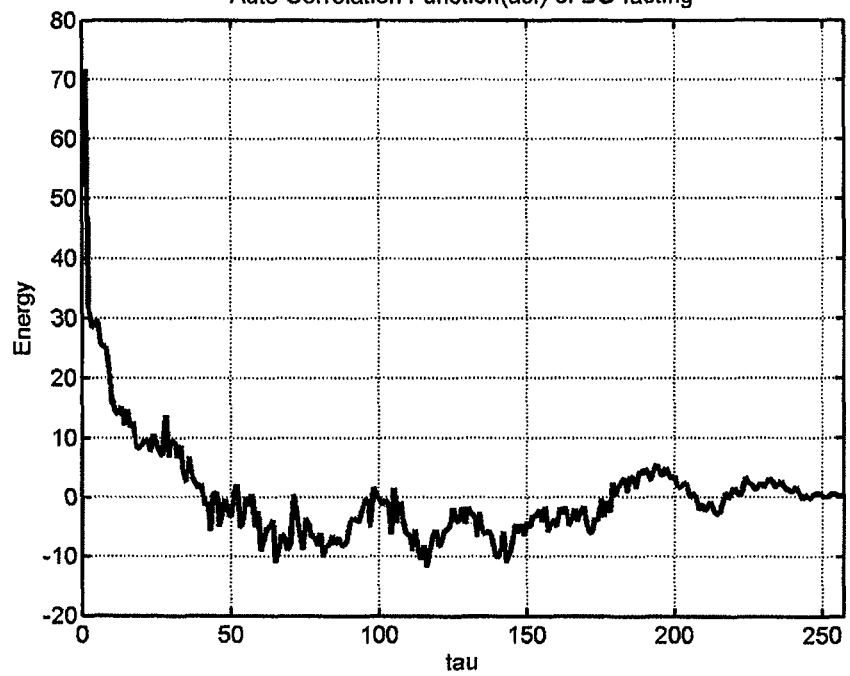
FIG. 6 shows an estimation of the autocorrelation function (acf) of the raw fasting BG-measurements (from the Case-Study). The acf is clearly indicating that there is a dependency over time in the signal.
Figure 7:
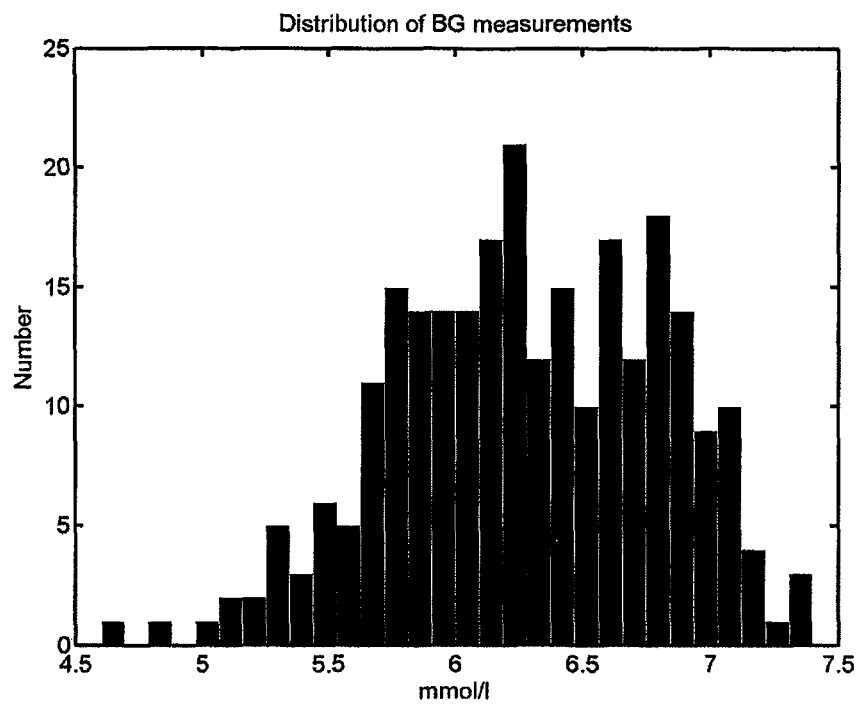
FIG. 7 shows a distribution histogram of the raw fasting BG-measurements, showing that they are approximately normal distributed.

Although measurements of BG seem to be extremely noisy it cannot be characterized as white noise. For clarification one can take a look at the estimated autocorrelation function (acf) where dependence is obvious (see FIG. 6 where the estimated acf is based on the inventors long-term fasting BG). The measurements, in this case study, are approximately normal distributed (see FIG. 7). If the measurements had larger variations it would most certainly be lognormal distributed.

Figure 8:
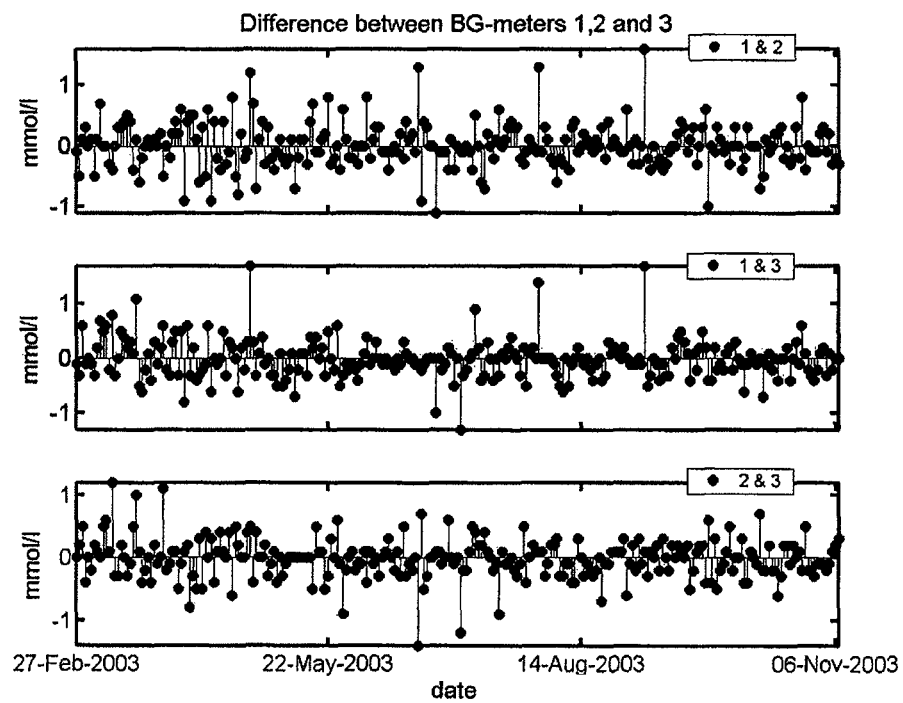
FIG. 8 shows measurement differences between BG-meter 1 & 2, 1 & 3 and 2 & 3 in the Case-Study.

Because of the inventor's measurement strategy, using three high quality BG-meters of the same brand, one can calculate the analytical error. This is being done by comparison of two BG meters at a time, which generates three approximately normal distributed cases with a standard deviation around 0.35 mmol/L (see FIG. 8). The data-series BG1, BG2 and BG3 generated by the three meters are independent of each other and $N(m, \sigma)$. $\overline{BG}$ is the arithmetic mean described by $$\overline{BG} \in N\left(m, \frac{\sigma}{\sqrt{n}}\right) \quad (1)$$

where the standard deviation $\sigma$ is approximately the same for each comparison, which are three to the number (n). By the use of the statistical rule that the variance of two normal distributed data-series are additive, we get $$\sqrt{2\sigma^2} \approx 0.35 \quad (2)$$

Hence, the standard deviation of the mean values of the three meters used in the case study is approximately 0.14 mmol/L.

Figure 9:
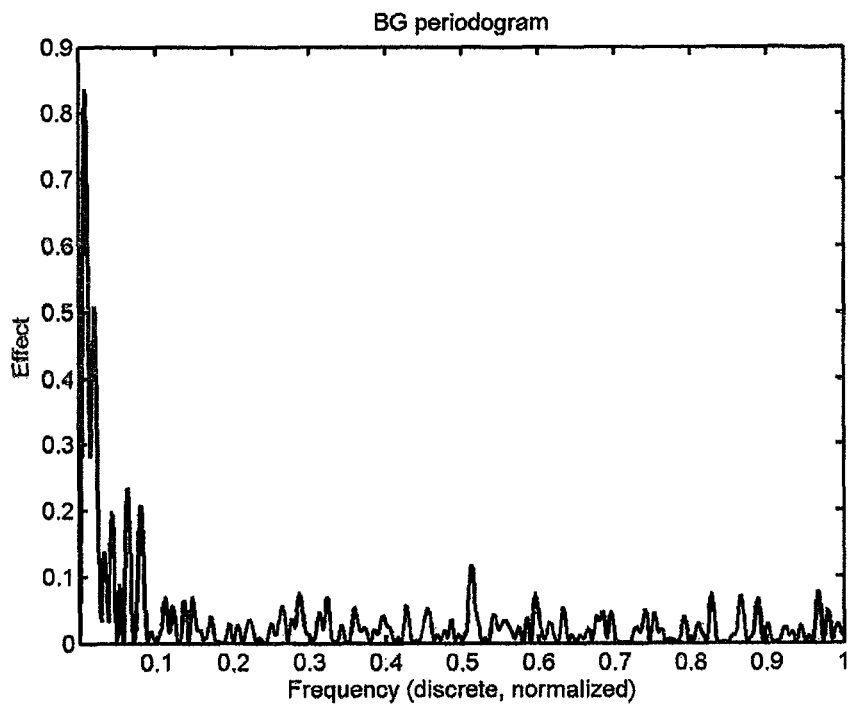
FIG. 9 shows the periodogram of raw fasting BG-measurements (from the Case-Study). Most energy is within the low frequency band. Hence, higher frequencies contain little or no useful information and may therefore be discarded.
Figure 10:
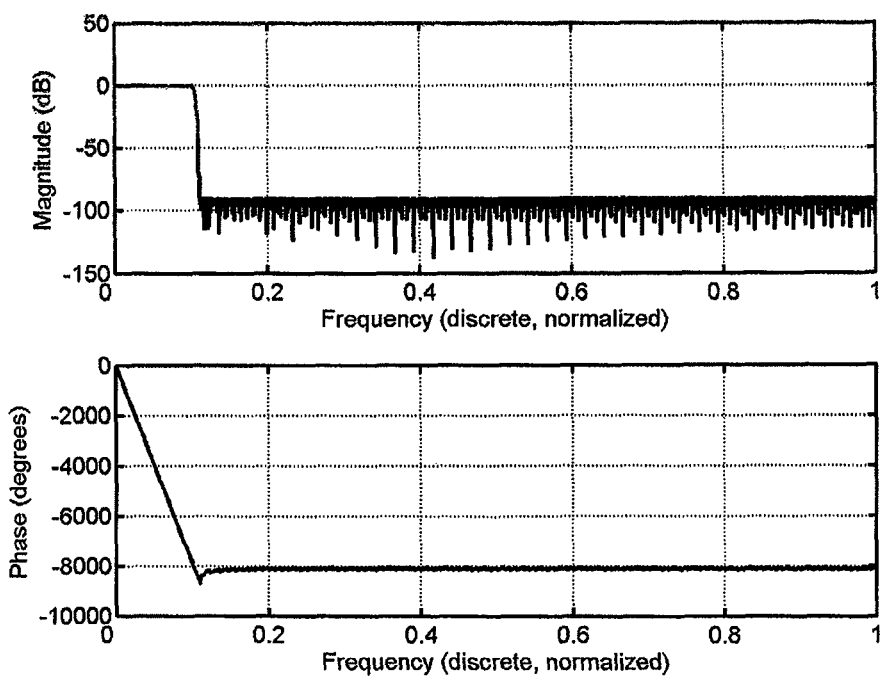
FIG. 10 shows the frequency response of the low-pass filter. Note that this cut-off frequency is a typical example.

To achieve a clear trend presentation of the noisy data it is necessary to process the data with a low-pass filter, which can be done through spectral analysis. In FIG. 9 the periodogram is shown where one can see that most energy is found within a low frequency band. The low-pass filtering is being processed by multiplication in the frequency domain $$S_{LP}(e^{j\omega}) = H(e^{j\omega}) \frac{1}{N} \sum_{t=1}^{N} BG(t) e^{-j\omega t} \quad (3)$$

where H is a FIR low-pass filter in the frequency domain (see FIG. 10 for frequency response for random picked cut-off frequency) and BG(t) raw measurements which are Fourier Transformed. $S_{LP}$ is then transformed back to the time domain via the inverse Fourier transform. Hence, residuals can be generated.

$$\Delta BG_{fd}(t) = BG(t) - BG_{LP(fd)}(t) \quad (4)$$

For a certain cut-off frequency fd between 0 and 1 (discrete frequency). When fd increases from 0 to 1 we can calculate the mean of the squared residuals, where N is the length of the residual vector for each value of fd.

$$\frac{1}{N}\sum_{t=1}^{N} \Delta BG(t)_0^2 \ldots \frac{1}{N}\sum_{t=1}^{N} \Delta BG(t)_1^2 \quad (5)$$

Figure 11:
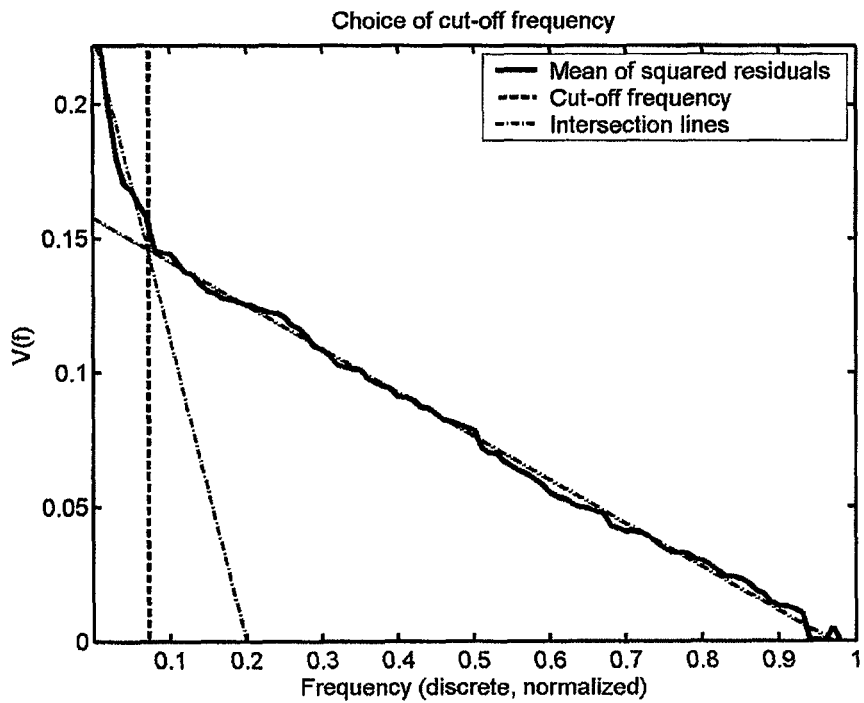
FIG. 11 shows that filtering the fasting BG-samples for cut-off frequencies between 0 and 1 generate residuals, or differences between raw samples and filtered samples. The mean value of the squared residuals, for each cut-off frequency, generates the curve in FIG. 11. This curve has a crossover break-point shown by two intersecting straight lines, indicating a suitable cut-off frequency being chosen.

This will generate a curve describing the behavior of the residuals for different fd (see FIG. 11). To find the most suitable cut-off frequency one should choose the frequency for the intersection in FIG. 11. The main purpose of the straight lines in FIG. 11 is to clarify the position of the residual-curve break. The same residual analysis can be applied to other biological measurements and signals. When the so designed low-pass filter processes the data, non-wanted high frequencies will be removed (see FIG. 12) by multiplying the zero-padded Fourier transforms of the LP-filter and the BG measurements.

Figure 1:
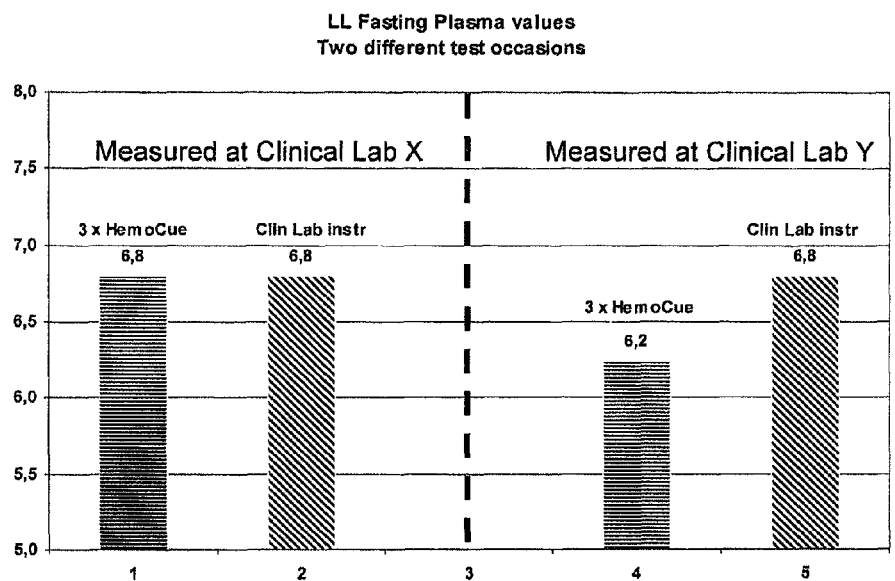
FIG. 1 shows fasting BG-measurements from two different occasions and clinics. Each occasion compares a lab-measurement with the mean of three measurements from three high quality BG-meters of the same brand. (Bar 1, 2 and 4 are expected to be correct).
Figure 2:
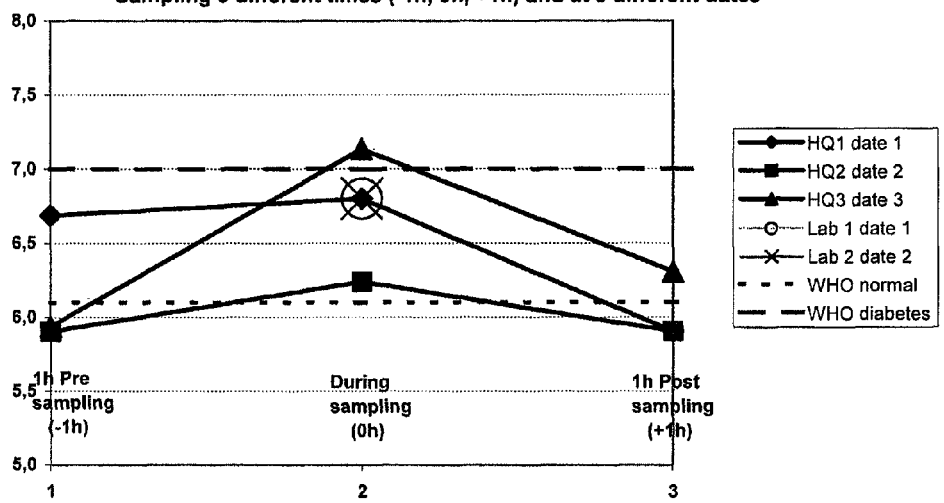
FIG. 2 shows the impact of "needle phobia", on three different test occasions, where the BG-value is rising substantially when the nurse is using a needle. The measurements are mean-values of three high quality BG-meters of the same brand.
Figure 3:
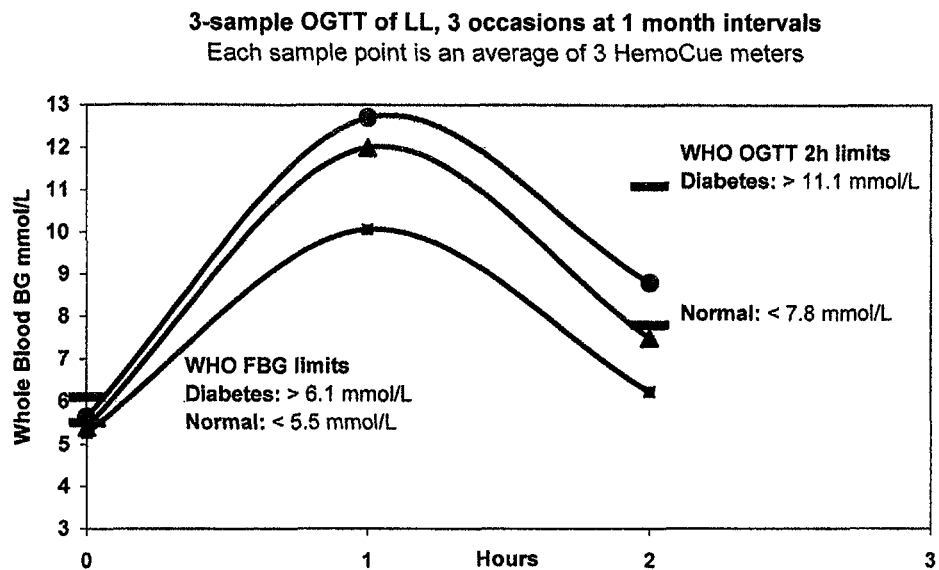
FIG. 3 shows three OGTT's from three different occasions. As few as only three samples can describe the BG-dynamics well.
Figure 4:
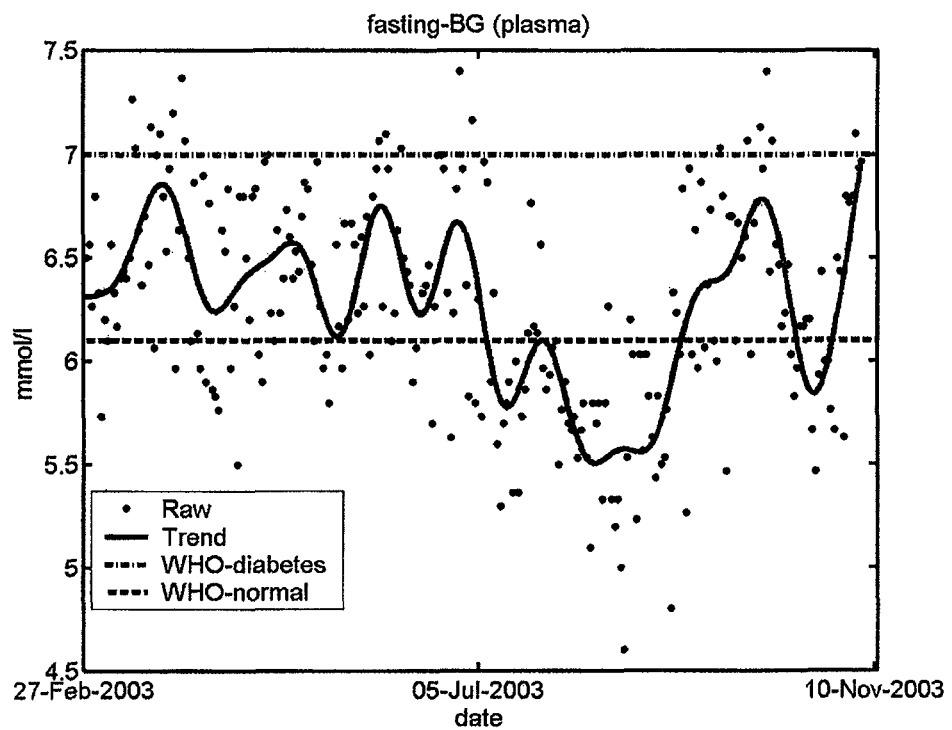
FIG. 4 shows raw fasting BG-measurements provided by the Case-Study (dots) together with the trend (low-pass filtered signal). WHO-limits are also presented.
Figure 5:
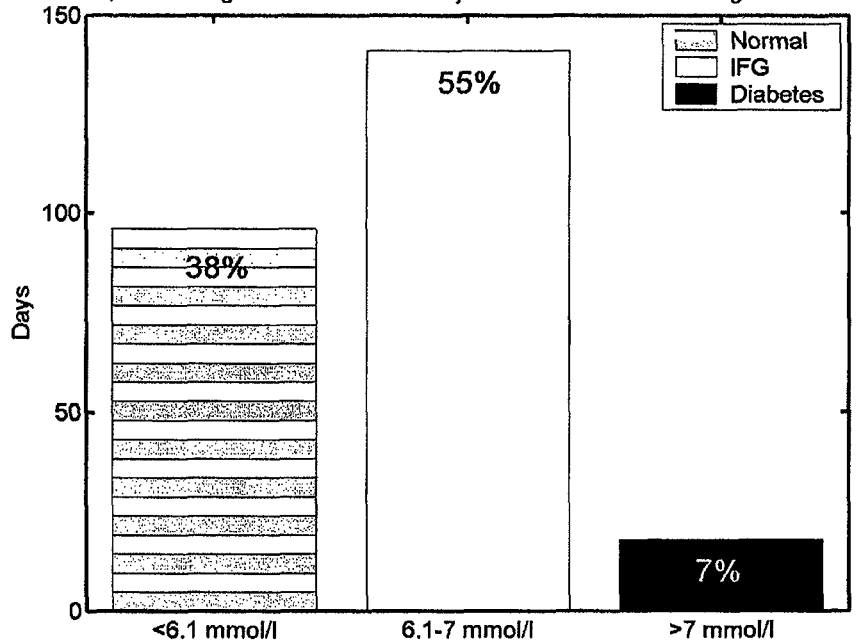
FIG. 5 shows that according to WHO-limits, there is a strong uncertainty in typical clinical BG-measurements as the diagnosis of the patient is very dependent on the occasion in time of the test.
Figure 12:
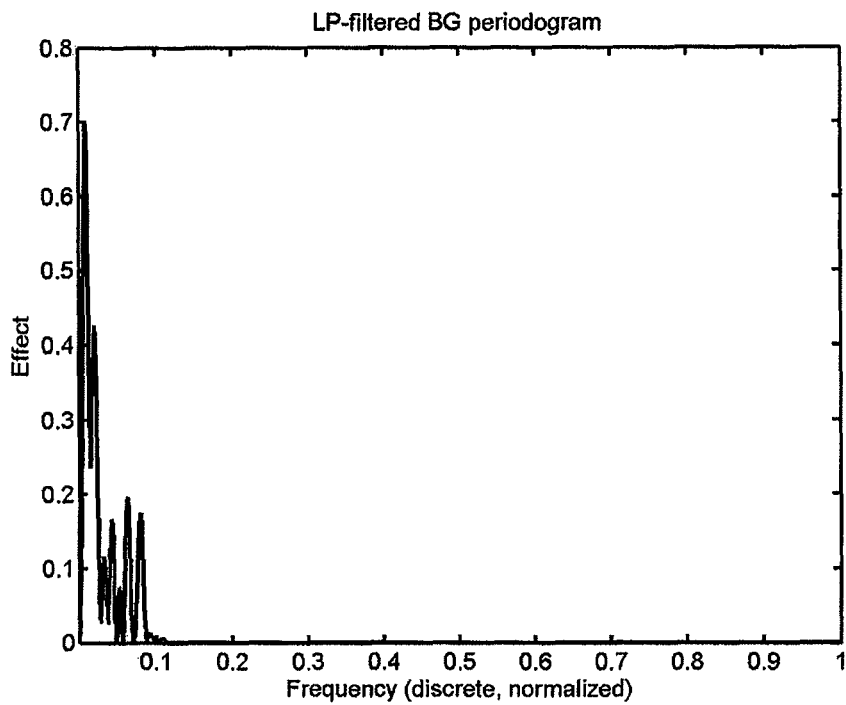
FIG. 12 shows a periodogram of fasting BG-samples being processed through a low-pass filter.

The result of the LP-filtering using the chosen cut-off frequency in the frequency domain and time domain, are shown in FIG. 12 and FIG. 4 respectively.

As an alternative one can perform similar filtering in the time-domain using convolution. Other types of low-pass filters may also be used by those skilled in the art.

Blood pressure can be measured at both arms and then low-pass filtered in order to reduce variance. Blood pressure can also be measured at the wrist, finger or other places. The Pulse-Wave-Transition-Time (PWTT) estimation can also be used to measure blood pressure. This estimates the blood pressure by measuring the pulse-wave transition time, starting from when the heart creates for example a EKG R-wave, to when the pulse-wave creates a light transmission difference due to changing blood pulse density, detected at a finger by a plethysmograph. In addition, from the systolic, diastolic and pulse data, it may be an advantage to calculate the Mean Arterial Pressure (MAP) and Pulse Pressure (PP) and present this data graphically.

In a similar manner, physical activity data is usually scattered due to large variations in daily activity or due to approximate estimations. It is therefore convenient to low-pass filter such data over time in a similar manner as above, as this makes the physical activity data easier to interpret. Physical activity can simply be estimated on an intensity scale where such scale can comprise the following grading of daily activities:

Very light (resting, reading, sitting, driving etc)
Light (walking, sweeping, playing piano, slow walk)
Moderate (fast walk, easy jogging, easy bicycling, skating, light weight training)
Hard (swimming, running, intense jogging, bicycle race, football, basketball etc)
Very hard (boxing, rowing, mountain climbing, intense weight training)

For more accurate estimation the MET (metabolic equivalent) can be used. 1 MET is equivalent to resting energy expenditure and light activity is <3 METS, moderate 3-5.9 METS, hard 6-8.9 METS or very hard>9 METS activity. MET activity tables are available to simplify calculation of calories burned (kcal), which is carried out by multiplying MET-value, weight and time elapsed. A cost-effective way of estimating physical activity is to use a pedometer. The activity data collected in the example graphs of the invention is using a pedometer that is used in combination with a built-in timer to calculate the approximate calories burned during the day or physical activity performed. It is practical to indicate energy expenditure as calories burned, as this is a commonly used and understandable term.

The heart rate data is also scattered due to large variations day to day. It is therefore convenient to low-pass filter such data in a similar manner as above, as this makes the heart rate data easier to interpret.

In an additional embodiment of the invention, systolic and diastolic blood pressure and heart rate is measured on a preferably daily basis in both arms. The data from both arms can then be averaged and low-pass filtered to reduce variability. The product of the systolic blood pressure and heart rate is calculated to obtain the Rate Pressure Product (RPP) in order to estimate the physical condition of the patient. RPP=Systolic BP*Heart rate/100. In addition to approximately indicate the oxygen utilization of the heart, the RPP reveals the presence of stimulating drugs like caffeine, nicotine, cocaine and amphetamine as well as mental and emotional stress. Thus the inventor teaches that the RPP is an important parameter to evaluate together with BG to establish the overall health-related condition of the patient. To achieve a trend presentation of RPP, as well as its separate components themselves, we can use a similar low-pass filter method, which produced the BG-trend. It may also be valuable for the physician to evaluate any blood pressure differences between the left and right arm, according to a separate long-term average of each arm.

Figure 13:
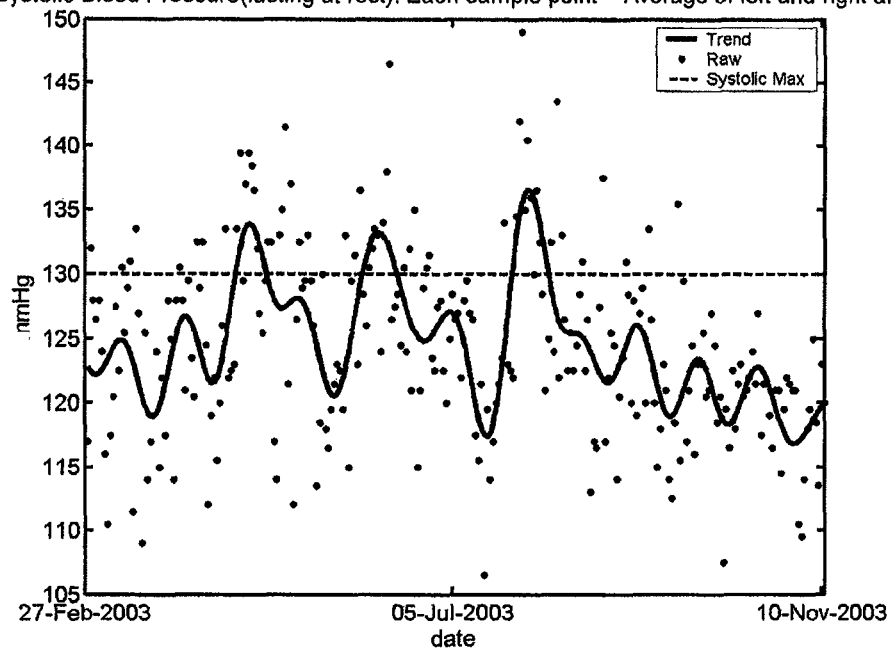
FIG. 13 shows raw systolic Blood Pressure samples together with its trend generated by the same method of low-pass filtering as above.

In a similar manner, the morning blood pressure data at rest is scattered due to large variations day to day and in addition due to analytic variability. Having the patient or doctor to make single-spot blood pressure measurements does not seem very meaningful according to the large noise level that also exists in the BP-data. It is therefore necessary to low-pass filter such data, as this makes the blood pressure data more accurate and easier to interpret, see FIG. 13.

Figure 14:
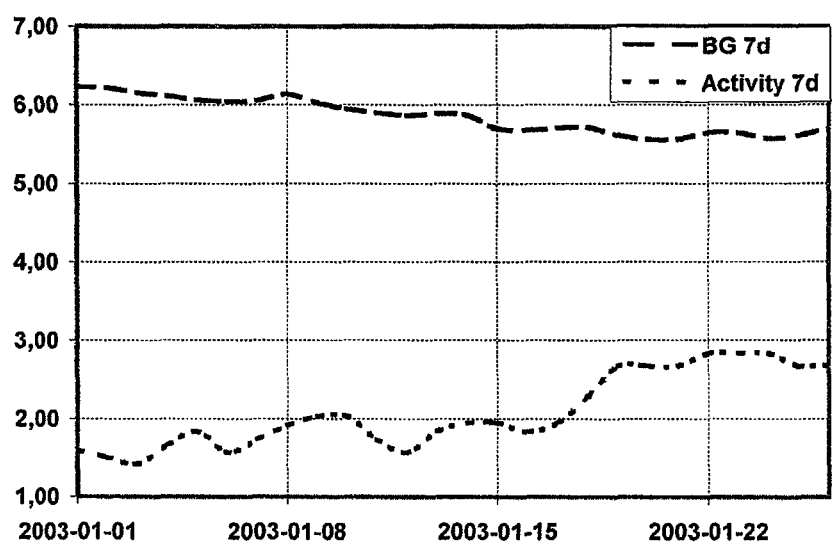
FIG. 14 shows trends of fasting BG and physical activity, indicating a correlation.

By simultaneously comparing the indicated data from the physical activity and BG-level filtered in an abovementioned way, it can be seen that an improvement in physical activity results in reduction in blood glucose level such as the blood glucose level is inversely proportional to physical activity. However, extreme physical activity can under certain conditions actually have the opposite effect, raising the blood glucose level. Thus by simultaneously presenting such data indicated for example graphically to the patient, he or she can easily adopt his effort of physical activity and other life style related efforts to suite a predefined target goal. This can now be achieved in an accurate and intuitive way, not needing to over-exaggerate the effort made, but instead simply working towards the blood glucose, RPP and activity target goal in a timely manner day-by-day as indicated by the progress in the graphics, see FIG. 14. It should be noted that new interesting de-correlations can also be observed in the graphs, see FIG. 15. For example when the patient has a flu or a virus infection, the BG value may rise unexpectedly and independently of the improved physical Activity. When increasing the physical activity, the BG value may also rise while the RPP decrease and the correlation become negative. Or when the patient encounters a stressful situation, the RPP may rise more than the BG. One could thus suspect a negatively correlated event under such conditions. Thus calculating the time-windowed correlation coefficient between RPP, BG and Activity and indicating this in the graphs, offers a new interesting indicator of patient status, and new conclusions can be drawn by an experienced user upon such negative correlation indications.

Figure 15:
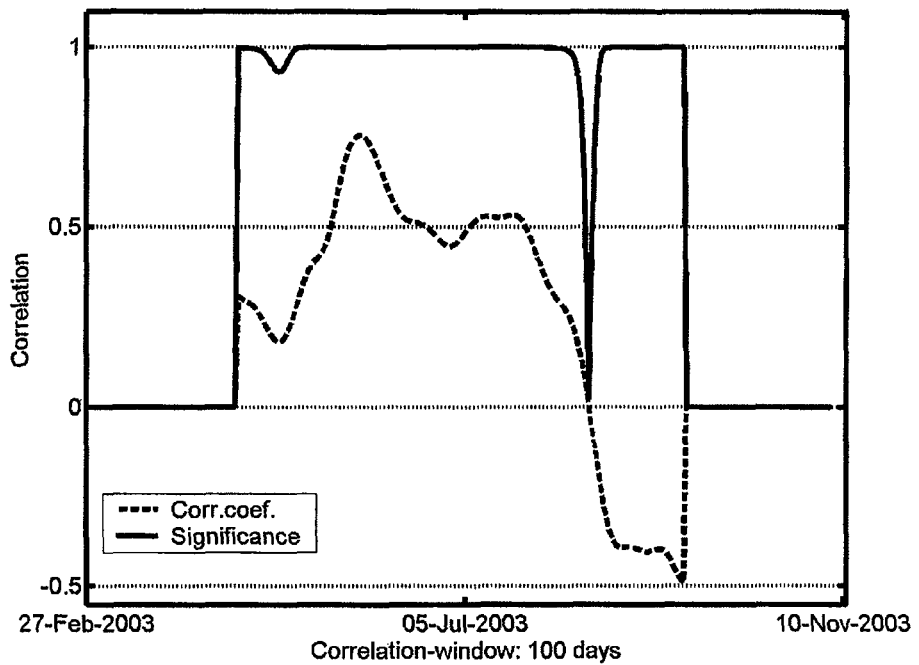
FIG. 15 shows correlation between BG- and RPP-trends (dotted line) generated by a rectangular moving window of 100 samples. Correlation significance (filled line, 1-P), should be >0.95 for significance.
Figure 16:
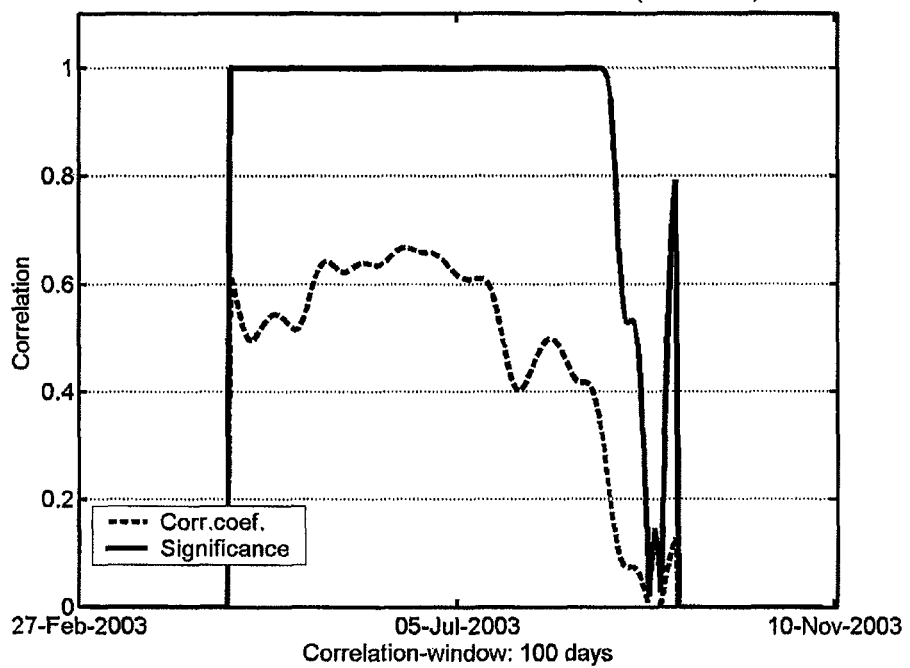
FIG. 16 shows correlation between BG- and RPP-trends derivatives (dotted line) generated by a rectangular moving window of 100 samples. Correlation significance (filled line, 1-P), should be >0.95 for significance.

In another embodiment of the invention a new method is presented where the inventor has discovered that the RPP dynamics correlates well with the BG dynamics and in inverse proportion to the level of physical activity and thus RPP may be used to predict BG fluctuations and dynamics, see FIG. 15 and FIG. 16.

In yet another embodiment of the invention the RPP can be used together with a predicting filter to calculate a surrogate measure for daily BG. This new BG prediction method can advantageously be used when it is not possible, impractical or felt painful and inconvenient by the patient to sample blood. Under such circumstances, BG measurements may be used only initially of the treatment or intervention period to calibrate the RPP predictor against the BG values. After such calibration is performed, the patient may revert to RPP measurements only, and take BG measurements for example only when visiting the doctor. In yet another embodiment of the invention, as described below, the BG-prediction filters are being updated on a sparse basis, for example once a week. Thus, initial training of the prediction filter first requires a data-sequence of densely sampled measurements. The length of this training sequence may be for example from one week to a month. Subsequently the prediction filter can be updated sparsely. The proposed prediction methods can be used to predict any signal x1 out of the signal x2, if a correlation is detected between x1 and x2 (note that x2 may be a combination of several measurement quantities).

Thus both BG and RPP can be used as an important indicators of improved self-control and life-style change in type 2-diabetes related disease. RPP shows a correlation to BG, and in particular under transitional phases of lifestyle changes, such as changing from sedentary lifestyle to a more active lifestyle or between varying intensity periods of physical activity. Thus the derivative of BG and derivative of RPP have a strong correlation (see FIG. 16). Under such circumstances the trends of both RPP and BG parameters change in a similar manner indicating high correlation. Under steady-state condition when the human is in "metabolic equilibrium" the correlation between RPP and BG may be less prominent due to excessive noise in the data from other metabolic processes. Thus the prediction filter is used to predict daily BG data from densely sampled RPP data. It needs to be mentioned that estimating BG by the use of the RPP is an economic and painless method as no, or only few blood glucose sticks or finger-pricking lances needs to be used. Measuring blood pressure for calculating the RPP does therefore not need any consumables as BG testing does. The proposed prediction method can be used also for other and future BG measurement methods where such methods are deemed cumbersome, impractical or uneconomical etc. Such methods may consist or measuring BG values from tear-liquid, from saliva or from instruments in contact with the skin etc.

The present invention predicts daily BG from the RPP at a high accuracy from the use of only sparsely sampled blood samples. The prediction may be proceeded by two different approaches, ARX and FIR-Wiener. As mentioned before, prediction methods require a sequence of data for training. Such sparsely sampled BG values are used to update an advanced filter predictor. Thus for the patient that has traumatic sensations from blood sampling or finger pricking, such painful activities can be reduced to for example one sample per week and still accurate daily BG values can be predicted by the predictor from the sparingly sampled BG values. The system is identified using transfer functions together with BG, an input signal x and white noise. x can be a vector of one variable or a matrix of several variables. Examples of variables can be measurements such as Rate Pressure Product, Systolic Blood Pressure, Diastolic Blood Pressure, Pulse, Mean Arterial Pressure, Pulse Pressure or Physical Activity.

This identification can be done since we are assuming that BG and x are partly affected by the same underlying parameters. Among these parameters we find for example physical activity, food habits, stress, virus and overweight. Therefore, we can present the system by the following hypothesis.

$$BG(t) = G(\theta, q)x(t) + H(\theta, q)e(t) \tag{6}$$

which is a description of a linear system where the noise part e(t) is a stochastic white noise with $E[e(t)]=0$. In a wider sense, the system can be described by the principles of a black box (see FIG. 17). G, and H are transfer functions and $\theta$ is a vector containing the polynomial-coefficients. Moreover, q is the shift operator. It is most preferable to use Rate Pressure Product since it has the highest correlation with BG. Therefore; the example below is using BG and RPP data.

An important pre-process when a system is being identified, is to subtract the mean value. This is given by $$\overline{BG} = \frac{1}{N}\sum_{t=1}^{N} BG(t), \tag{7}$$

$$\overline{RPP} = \frac{1}{N}\sum_{t=1}^{N} RPP(t)$$

where N is the number of measurements. There are several ways to estimate the transfer functions $G(\theta, q)$ and $H(\theta, q)$, where models like ARX, ARMAX, OE and Box-Jenkins can be mentioned. In this case ARX is discussed, which provides a straightforward prediction algorithm called linear regression. Box-Jenkins is the most complex model which the other models are being special cases of. Tests have shown minimum amount of differences between the different model-approaches.

The ARX-model can be written as $$BG(t) + a_1 BG(t-1) + \ldots + a_{n_a} BG(t-n_a) = b_1 RPP(t-1-nk) + \ldots + b_{n_b} RPP(t-n_b-nk+1) + e(t) \tag{8}$$

where the polynomial-coefficients can be collected and written as $$\theta = [a_1 \ldots a_{n_a} b_1 \ldots b_{n_b}]^T \tag{9}$$

Furthermore, equation 2 can be rewritten as $$A(q)BG(t) = B(q)RPP(t-nk) + e(t) \tag{10}$$

where $$G(q, \theta) = \frac{B(q)}{A(q)} \tag{11}$$

and $$H(q, \theta) = \frac{1}{A(q)}$$

nk is the delay.

Given the optimal elements in the vector $\theta$, old BG- and RPP values, it is possible to predict BG. The prediction is being calculated with knowledge of $\theta$ and the regression vector $\phi$, containing old BG and RPP values.

$$\phi(t) = [-BG(t-1) \ldots -BG(t-n_a) RPP(t-nk) \ldots RPP(t-n_k-n_b+1)]^T \tag{12}$$

Note that the noise term e(t) is not a member of $\phi$. Furthermore, the product of $\theta$ and $\phi$ provides the prediction $$\hat{BG}(t|\theta) = \theta^T \phi(t) \tag{13}$$

In the example the predictor is designed as a one-step predictor, and becomes adaptive as it retrains for every prediction. Other step lengths of predictors and other types of predictors can be used by those skilled in the art.

For each calculation of θ at the time t−1, a guess or a prediction of BG(t) will be produced. Hence, at the time t it is possible to carry out the prediction error $$\epsilon(t,\theta) = BG(t) - \hat{B}\hat{G}(t|\theta) \quad (14)$$

For a training sequence of the length N we get the quadratic criteria $$V_N(\theta) = \frac{1}{N}\sum_{t=1}^{N} \epsilon^2(t,\theta) \quad (15)$$

It is therefore straight forward to pick the θ, which gives $$\hat{\theta}_N = \underset{\theta}{\operatorname{argmin}}\, V_N(\theta) \quad (16)$$

("arg min" is the minimized argument)

We have the prediction error $$\epsilon(t,\theta) = BG(t) - \theta^T \varphi(t) \quad (17)$$

Hence, the quadratic criteria (11) can be written as $$\begin{aligned}V_N &= \frac{1}{N}\sum_{t=1}^{N}(BG(t)-\theta^T\varphi(t))^2 \\ &= \frac{1}{N}\sum_{t=1}^{N} BG^2(t) - \frac{1}{N}\sum_{t=1}^{N} 2\theta^T\varphi(t)BG(t) + \\ &\quad \frac{1}{N}\sum_{t=1}^{N}\theta^T\varphi(t)\varphi^T(t)\theta \\ &= \frac{1}{N}\sum_{t=1}^{N} BG^2(t) - 2\theta^T f_N + \theta^T R_N \theta \end{aligned} \quad (18)$$

where $$f_N = \frac{1}{N}\sum_{t=1}^{N}\varphi(t)BG(t) \quad (19)$$

and $$R_N = \frac{1}{N}\sum_{t=1}^{N}\varphi(t)\varphi^T(t) \quad (20)$$

If $R_N$ is invertible, the formula can be written as $$V_N = \frac{1}{N}\sum_{t=1}^{N} BG^2(t) - f_N^T R_N^{-1} f_N + (\theta - R_N^{-1} f_N)^T R_N (\theta - R_N^{-1} f_N) \quad (21)$$

The last part of (19) is always zero if $$\theta = \hat{\theta}_N = R_N^{-1} f_N \quad (22)$$

and because $R_N$ is positive definite, this provides a minimum. Hence, the optimal minimized value of $V_N(\theta)$ is given when equation (22) is fulfilled, because the rest of the terms are independent of θ. To improve this predictor one can use the information of residuals, which will be available when a true BG-sample is being taken. This residual can be weighted exponentially in order to be added to forthcoming predictions for improved amplitude tracking.

Figure 18:
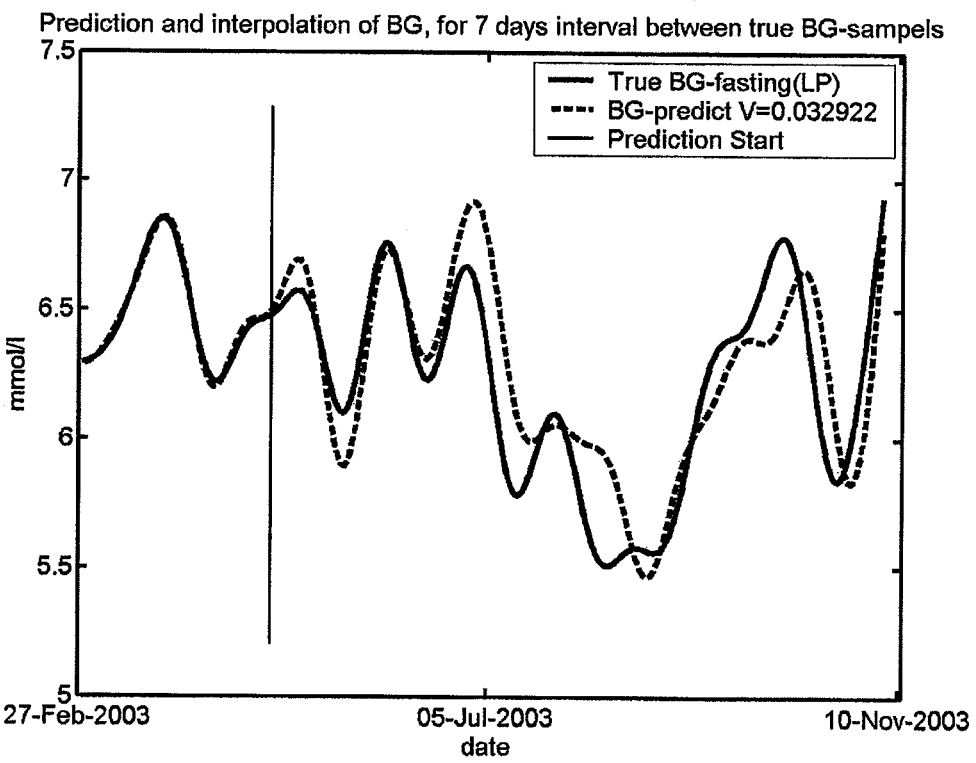
FIG. 18 shows the result of low-pass filtered BG-prediction. The prediction filter is in this example being updated every seventh day.

As an example, FIG. 18 show the results of the predictor when it is being updated with true BG-samples only every 7:th day. In another embodiment of the invention the predictor may free-run and updated only initially by a short BG-sequence.

As another prediction example one can implement a FIR-Wiener filter, which is a powerful predictor suppressing noise optimally. A variable describing future BG-samples can be written as (of course BG is just an example in this matter, one can replace BG with some other sparse sampled variable being correlated with the densely sampled variable). Hence, we create the predicted value BG as.

$$x_k = BG(n+k) \quad (23)$$

We create a vector containing BG- and RPP-measurements.

$$y = [BG(n)\ldots BG(n-tM)RPP(n+k)\ldots RPP(n-T+k)] \quad (24)$$

where t is the number of old BG-values in and M is the testing interval of BG. T represents old values of RPP while k is the number of steps being predicted (k<M).

Further, we estimate a matrix containing auto-correlation functions and cross-correlation functions. In order to calculate these estimations we can use a sequence of known measurements, as a training sequence.

$$\hat{R}_{yy} = E[y^T y] \quad (25)$$

We also estimate the cross-correlation $$r_{xy} = E[x_k y^T] \quad (26)$$

Now the filter can be created as, (one for each prediction, k is an index of the prediction step)

$$h_k = \hat{R}_{yy}^{-1} r_{xy} \quad (27)$$

Which leads to the predicted value $$\hat{B}\hat{G}(n+k) = h_k y^T \quad (28)$$

Analysis of the time series data for relevance should be performed and data dropouts or outliers above a threshold can be substituted using averages of neighbouring data. This is most important, as it is normal to sometimes forget to take measurements or sometimes make errors in manual interpretation of measurements. Long data dropouts may need to be interpolated in such situation when the subject has forgotten his device or when gone for a holiday etc. The linear interpolation is also an alternative to the linear regression prediction method. For example, if BG measurements are being taken once every week, the vector of known BG-data is a down sampled version of an every day sampled BG vector. This can be described as $$BG_M(n) = BG(nM) \quad (29)$$

for any interpolation interval M days (or samples). The linear interpolation is then carried out by applying a straight line based on M−1 samples between the elements in $BG_M$. As an example, FIG. 18 shows the results of the interpolator with true BG-samples every 7:th day. Linear interpolation also can be carried out for non-equidistant dates with missing data.

Further, in another embodiment of the invention it may be preferable to automatically switch between linear interpolation and prediction, based on the sequence of missing data. The appropriate point in time of the switch-over may be determined by residual analysis of past known data. The residuals are generated from two cases: Case 1 where linear interpolated data in a certain sequence are compared with raw data. Case 2 where predicted data in the very same sequence are compared with raw data. This is of course being done in the same interval/sequence providing useful comparison between the two cases. The goal is to keep the residuals as small as possible and therefore the switchover point may be determined where the mean of the squared residuals from two cases intersect.

Figure 19:
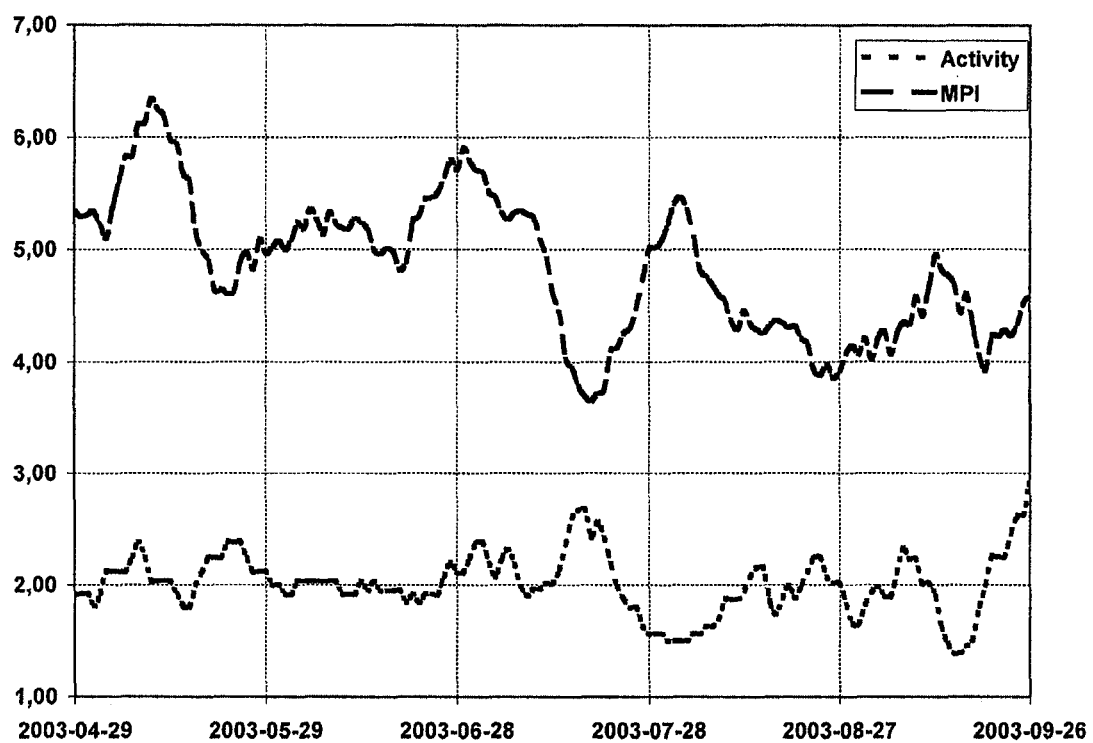
FIG. 19 shows trends of the Metabolic Performance Index and physical activity, indicating a correlation.

The sum or factorisation of BG and RPP may be used as a metabolic performance indicator called the Metabolic Performance Index (MPI) by the inventor, an indicator that may span a number of abnormalities and disease, thus a clear indicator for the promotion of self control and life-style change in type 2-diabetes related disease, see FIG. 19. Early indications show that the MPI indicator may also be used with advantage in sports training events for athletes etc.

It is believed by the inventor that a metabolic monitoring and indication device according to the proposed invention will be a very valuable asset to the patient for self management as well as a new tool for the physician to clearly and accurately assess and follow up patient status, and as such can be used as a valuable treatment tool. A screen-shot of a version of the software product is shown in FIG. 20. It is also believed that this multiparameter metabolic monitoring and indication device can be used to monitor physical status and progress of any human such as a sports athletic like a runner or swimmer etc, and for any mammalian such a race horse or racing dog, where its trainer can make positive use of the output data to guide further training and improve performance.

As an alternative to new hardware development, standard proven technologies and mass-produced consumer medical monitoring instruments may be used for data collection where a computer program product and a computer (desk-top, lap-top, palm-top or smart-phone) can be used to collect, download, analyse and present the information in a practical and intuitive way. In addition, intelligent blood-glucose monitors can be built or intelligent combination apparatus of blood-glucose and blood pressure monitor including a microprocessor and accelerometer for physical activity and a screen for display. The present invention can be implemented both in software, hardware chips and DSPs, for various kinds of use, for computation, storage and/or transmission of the signals, analogue or digital.

The described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

The invention claimed is:

1. An apparatus for indicating a health-related condition of a subject, comprising:
   an input interface for receiving a raw sequence of samples of a biological quantity derived by a measurement method and a further raw sequence of a different biological quantity derived by a further measurement method;
   a first processor for processing the raw sequence of samples to obtain a processed sequence, the first processor comprising an interpolator for providing data on an interpolated sample for a missing sample of the biological quantity using one or more samples at a preceding time instant or one or more samples at a subsequent time instant to obtain an interpolated sequence representing samples of the raw sequence and the interpolated sample;
   a filter for filtering the processed sequence provided by the first processor to obtain a filtered sequence, the filtered sequence having a useful variation and a reduced non-useful variation compared to the processed sequence before filtering, wherein the filter is configured for filtering the further raw sequence to obtain a further filtered sequence;
   an output interface for processing an enhanced sequence derived from the filtered sequence and for outputting at least an increase indication, a decrease indication or a remain unchanged indication as a trend of the enhanced sequence, the trend being representative of a useful variation of the health-related condition of the subject; and
   a second processor for deriving the enhanced sequence from the filtered sequence, wherein the second processor comprises a combiner, for combining the filtered sequence and the further filtered sequence to derive the enhanced sequence.

2. Apparatus in accordance with claim 1, in which the measurement method is a blood or plasma glucose measurement, and
   in which the further measurement method is a heart rate measurement, a blood pressure measurement or a method for obtaining a product of heart rate and blood pressure.

3. Apparatus in accordance with claim 1, in which the combiner is arranged for performing a sample-wise multiplication.

4. Apparatus in accordance with claim 1, in which the biological quantity is a blood glucose level, a blood lipid level or a blood insulin level of the subject.

5. Apparatus in accordance with claim 1, in which the health-related condition is a diabetes-related or glucose-related or insulin-related metabolic disorder.

6. Apparatus in accordance with claim 1, in which the filter is a low-pass filter and has a cut-off frequency, which is set such that the low frequency energy for frequencies of the raw sequence or the processed sequence provided by the first processor has a predetermined portion of a total energy of the raw sequence or the processed sequence.

7. Apparatus in accordance with claim 6, further comprising a cut-off frequency calculator being arranged to determine the cut-off frequency, using;
   determining different cut-off frequencies for a low-pass filter for filtering the samples to obtain filtered test signals;
   for each filtered test signal, deriving residual values based on the difference of the raw sequence and a filtered test signal to obtain a residual representation;
   based on the residual representation, determining a cut-off frequency individually adapted to the raw sequence of samples.

8. Apparatus in accordance with claim 7, in which the cut-off frequency calculator is arranged to determine the cut-off frequency by:
   determining a first line using residual energies for low cut-off frequencies;
   determining a second line using residual energies for high cut-off frequencies; and finding an intersection point of the first line and the second line, the intersection point indicating the cut-off frequency.

9. Apparatus in accordance with claim 1, in which the output interface is arranged to indicate the trend by an acoustic indicator, an optical indicator or a mechanical indicator, so that the decrease indication, the increase indication or the remain unchanged indication are acoustically, optically or mechanically different from each other.

10. Apparatus in accordance with claim 1, in which the output interface is arranged to derive and output the trend from an actual value of the enhanced sequence, and a timely preceding value of the filtered sequence or the enhanced sequence.

11. A method for indicating a health-related condition of a subject, comprising:
receiving, at an input interface, a raw sequence of samples of a biological quantity derived by a measurement method and a further raw sequence of a different biological quantity derived by a further measurement method;
processing the raw sequence of samples using a processor to obtain a processed sequence, comprising providing data on an interpolated sample for a missing sample of the biological quantity using one or more samples at a preceding time instant or one or more samples at a subsequent time instant to obtain an interpolated sequence representing samples of the raw sequence and the interpolated sample;
filtering the processed sequence, which was obtained by said processing of the raw sequence of samples, using a filter to obtain a filtered sequence, the filtered sequence having a useful variation and a reduced non-useful variation compared to the processed sequence before filtering and filtering the further raw sequence to obtain a further filtered sequence;
processing an enhanced sequence derived from the filtered sequence by combining it with the further filtered sequence, and outputting, at an output interface, at least an increase indication, a decrease indication or a remain unchanged indication as a trend of the enhanced sequence, the trend being representative of a useful variation of the health-related condition of the subject.

12. A non-transitory digital storage medium having stored thereon a computer program having a program code for performing a method for indicating a health-related condition of a subject, the method comprising:
receiving a raw sequence of samples of a biological quantity derived by a measurement method and a further raw sequence of a different biological quantity derived by a further measurement method;
processing the raw sequence of samples to obtain a processed sequence, comprising providing data on an interpolated sample for a missing sample of the biological quantity using one or more samples at a preceding time instant or one or more samples at a subsequent time instant to obtain an interpolated sequence representing samples of the raw sequence and the interpolated sample;
filtering the processed sequence to obtain a filtered sequence, the filtered sequence having a useful variation and a reduced non-useful variation compared to the processed sequence before filtering and filtering the further raw sequence to obtain a further filtered sequence; and
processing an enhanced sequence derived from the filtered sequence by combining it with the further filtered sequence, and outputting at least an increase indication, a decrease indication or a remain unchanged indication as a trend of the filtered sequence or the enhanced sequence, the trend being representative of a useful variation of the health-related condition of the subject, when the computer program is running on a computer.

13. An apparatus for indicating a health-related condition of a subject, comprising:
an input interface for receiving a raw sequence of samples of a biological quantity derived by a measurement method and a further raw sequence of a different biological quantity derived by a further measurement method;
a processor for processing the raw sequence of samples to obtain a processed sequence, the processor comprising:
an interpolator for providing data on an interpolated sample for a missing sample of the biological quantity using one or more samples at a preceding time instant or one or more samples at a subsequent time instant to obtain an interpolated sequence representing samples of the raw sequence and the interpolated sample; and
a combiner for combining the raw sequence and the further raw sequence to obtain a combined raw sequence to be filtered by the filter;
a filter for filtering the combined raw sequence to obtain a filtered sequence, the filtered sequence having a useful variation and a reduced non-useful variation compared to the processed sequence before filtering; and
an output interface for processing the filtered sequence or for processing an enhanced sequence derived from the filtered sequence and for outputting at least an increase indication, a decrease indication or a remain unchanged indication as a trend of the filtered sequence or the enhanced sequence, the trend being representative of a useful variation of the health-related condition of the subject.

14. Apparatus in accordance with claim 13, in which the measurement method is a blood or plasma glucose measurement, and
in which the further measurement method is a heart rate measurement, a blood pressure measurement or a method for obtaining a product of heart rate and blood pressure.

15. Apparatus in accordance with claim 13, in which the combiner is arranged for performing a sample-wise multiplication.

16. Apparatus in accordance with claim 13, in which the biological quantity is a blood glucose level, a blood lipid level or a blood insulin level of the subject.

17. Apparatus in accordance with claim 13, in which the health-related condition is a diabetes-related or glucose-related or insulin-related metabolic disorder.

18. Apparatus in accordance with claim 13, in which the filter is a low-pass filter and has a cut-off frequency, which is set such that the low frequency energy for frequencies of a raw sequence or a processed sequence has a predetermined portion of a total energy of the raw sequence or the processed sequence.

19. Apparatus in accordance with claim 18, further comprising a cut-off frequency calculator being arranged to determine the cut-off frequency, using;
determining different cut-off frequencies for a low-pass filter for filtering the samples to obtain filtered test signals;
for each filtered test signal, deriving residual values based on the difference of the raw sequence and a filtered test signal to obtain a residual representation;

based on the residual representation, determining a cut-off frequency individually adapted to the raw sequence of samples.

20. Apparatus in accordance with claim 19, in which the cut-off frequency calculator is arranged to determine the cut-off frequency by:
- determining a first line using residual energies for low cut-off frequencies;
- determining a second line using residual energies for high cut-off frequencies; and
- finding an intersection point of the first line and the second line, the intersection point indicating the cut-off frequency.

21. Apparatus in accordance with claim 13, in which the output interface is arranged to indicate the trend by an acoustic indicator, an optical indicator or a mechanical indicator, so that the decrease indication, the increase indication or the remain unchanged indication are acoustically, optically or mechanically different from each other.

22. Apparatus in accordance with claim 13, in which the output interface is arranged to derive and output the trend from an actual value of the filtered sequence or the enhanced sequence, and a timely preceding value of the filtered sequence or the enhanced sequence.

23. A method for indicating a health-related condition of a subject, comprising:
- receiving, at an input interface, a raw sequence of samples of a biological quantity derived by a measurement method and a further raw sequence of a different biological quantity derived by a further measurement method;
- combining the raw sequence and the further raw sequence using a combiner to obtain a combined raw sequence;
- processing the combined raw sequence of samples using a processor to obtain a processed sequence, comprising providing data on an interpolated sample for a missing sample of the biological quantity using one or more samples at a preceding time instant or one or more samples at a subsequent time instant to obtain an interpolated sequence representing samples of the combined raw sequence and the interpolated sample;
- filtering the processed sequence using a filter to obtain a filtered sequence, the filtered sequence having a useful variation and a reduced non-useful variation compared to the processed sequence before filtering; and
- processing the filtered sequence or processing an enhanced sequence derived from the filtered sequence and outputting, at an output interface, at least an increase indication, a decrease indication or a remain unchanged indication as a trend of the filtered sequence or the enhanced sequence, the trend being representative of a useful variation of the health-related condition of the subject.

24. A non-transitory digital storage medium having stored thereon a computer program having a program code for performing a method for indicating a health-related condition of a subject, the method comprising:
- receiving a raw sequence of samples of a biological quantity derived by a measurement method and a further raw sequence of a different biological quantity derived by a further measurement method;
- combining the raw sequence and the further raw sequence to obtain a combined raw sequence;
- processing the combined raw sequence of samples to obtain a processed sequence, comprising providing data on an interpolated sample for a missing sample of the biological quantity using one or more samples at a preceding time instant or one or more samples at a subsequent time instant to obtain an interpolated sequence representing samples of the combined raw sequence and the interpolated sample;
- filtering the processed sequence to obtain a filtered sequence, the filtered sequence having a useful variation and a reduced non-useful variation compared to the processed sequence before filtering; and
- processing the filtered sequence or processing an enhanced sequence derived from the filtered sequence and outputting at least an increase indication, a decrease indication or a remain unchanged indication as a trend of the filtered sequence or the enhanced sequence, the trend being representative of a useful variation of the health-related condition of the subject, when the computer program is running on a computer.

* * * * *

UNITED STATES PATENT AND TRADEMARK OFFICE
CERTIFICATE OF CORRECTION

PATENT NO. : 8,858,435 B2
APPLICATION NO. : 12/842831
DATED : October 14, 2014
INVENTOR(S) : Lars Gustaf Liljeryd and Ulf Frederik Magnusson It is certified that error appears in the above-identified patent and that said Letters Patent is hereby corrected as shown below:

Claims

Column 22, Claim 7, line 50:
... arranged to determine the cut-off frequency, using;
should read
... arranged to determine the cut-off frequency, using:

Column 23, Claim 11, line 23:
sorto obtain...
should read:
sor to obtain...

Column 24, Claim 12, line 2:
as a trend of the filtered sequence or the enhanced
should read:
as a trend of the enhanced Column 24, Claim 19, line 60:
... arranged to determine the cut-off frequency, using;
should read
... arranged to determine the cut-off frequency, using:

Signed and Sealed this
Second Day of February, 2016

Michelle K. Lee
*Director of the United States Patent and Trademark Office*